(12) United States Patent
Jalali et al.

(10) Patent No.: US 12,395,015 B1
(45) Date of Patent: Aug. 19, 2025

(54) OPTICAL POWER DELIVERY TO IMPLANTED MEDICAL DEVICES

(71) Applicant: Seaford Holdings, LLC, El Segundo, CA (US)

(72) Inventors: Bahram Jalali, Los Angeles, CA (US); Koichiro Kishima, Yokohama (JP); William R Ryan, Los Angeles, CA (US); Ahmadreza Rofougaran, Newport Coast, CA (US)

(73) Assignee: Wireless Photonics, LLC, El Segundo, CA (US)

( * ) Notice: Subject to any disclaimer, the term of this patent is extended or adjusted under 35 U.S.C. 154(b) by 0 days.

(21) Appl. No.: 19/072,089

(22) Filed: Mar. 6, 2025

Related U.S. Application Data

(60) Provisional application No. 63/755,437, filed on Feb. 7, 2025.

(51) Int. Cl.
| | |
|---|---|
| *H02J 50/30* | (2016.01) |
| *A61M 5/142* | (2006.01) |
| *A61N 1/372* | (2006.01) |
| *A61N 1/378* | (2006.01) |
| *H02J 50/80* | (2016.01) |

(52) U.S. Cl.
CPC ......... *H02J 50/30* (2016.02); *A61M 5/14276* (2013.01); *A61N 1/37217* (2013.01); *A61N 1/3787* (2013.01); *H02J 50/80* (2016.02); *A61M 2205/04* (2013.01); *A61M 2205/3327* (2013.01); *A61M 2205/3368* (2013.01); *A61M 2205/3523* (2013.01); *A61M 2205/3561* (2013.01); *A61M 2205/8206* (2013.01); *A61M 2205/8237* (2013.01); *H02J 2310/23* (2020.01)

(58) Field of Classification Search
CPC ........ H02J 50/30; H02J 50/80; H02J 2310/23; A61M 5/14276; A61N 1/37217; A61N 1/3787
USPC .......................................... 307/149
See application file for complete search history.

(56) References Cited

U.S. PATENT DOCUMENTS

| | | | | |
|---|---|---|---|---|
| 12,136,814 | B1* | 11/2024 | Jalali | H02J 13/00034 |
| 2004/0212344 | A1* | 10/2004 | Tamura | H02J 7/0044 |
| | | | | 320/114 |
| 2004/0266367 | A1* | 12/2004 | Tuominen | H04B 10/807 |
| | | | | 455/91 |
| 2019/0229558 | A1* | 7/2019 | Pigeon | A61N 1/3787 |
| 2020/0382198 | A1* | 12/2020 | Ashrafi | H04B 7/155 |
| 2020/0403457 | A1* | 12/2020 | Nydell | H10F 77/488 |
| 2023/0016800 | A1* | 1/2023 | Nugent, Jr. | H02J 50/005 |

\* cited by examiner

*Primary Examiner* — Alfonso Perez Borroto
(74) *Attorney, Agent, or Firm* — Mark R. Kendrick

(57) ABSTRACT

An optical wireless power delivery system to provide power to a medical implant device includes a battery pack, a flexible adhesive device and a medical implant assembly. The flexible adhesive device is attached a subject's skin and include a port to receive electrical power from the battery pack and to power the one or more LED light assemblies that transmit a plurality of light beams to a skin or tissue of the subject. The medical implant assembly has a photovoltaic assembly to receive the plurality of light beams and convert the plurality of light beams to electrical power. The electrical power is transferred to the battery charger controller, which charges the rechargeable battery and provides electrical power to the medical implant device.

20 Claims, 13 Drawing Sheets

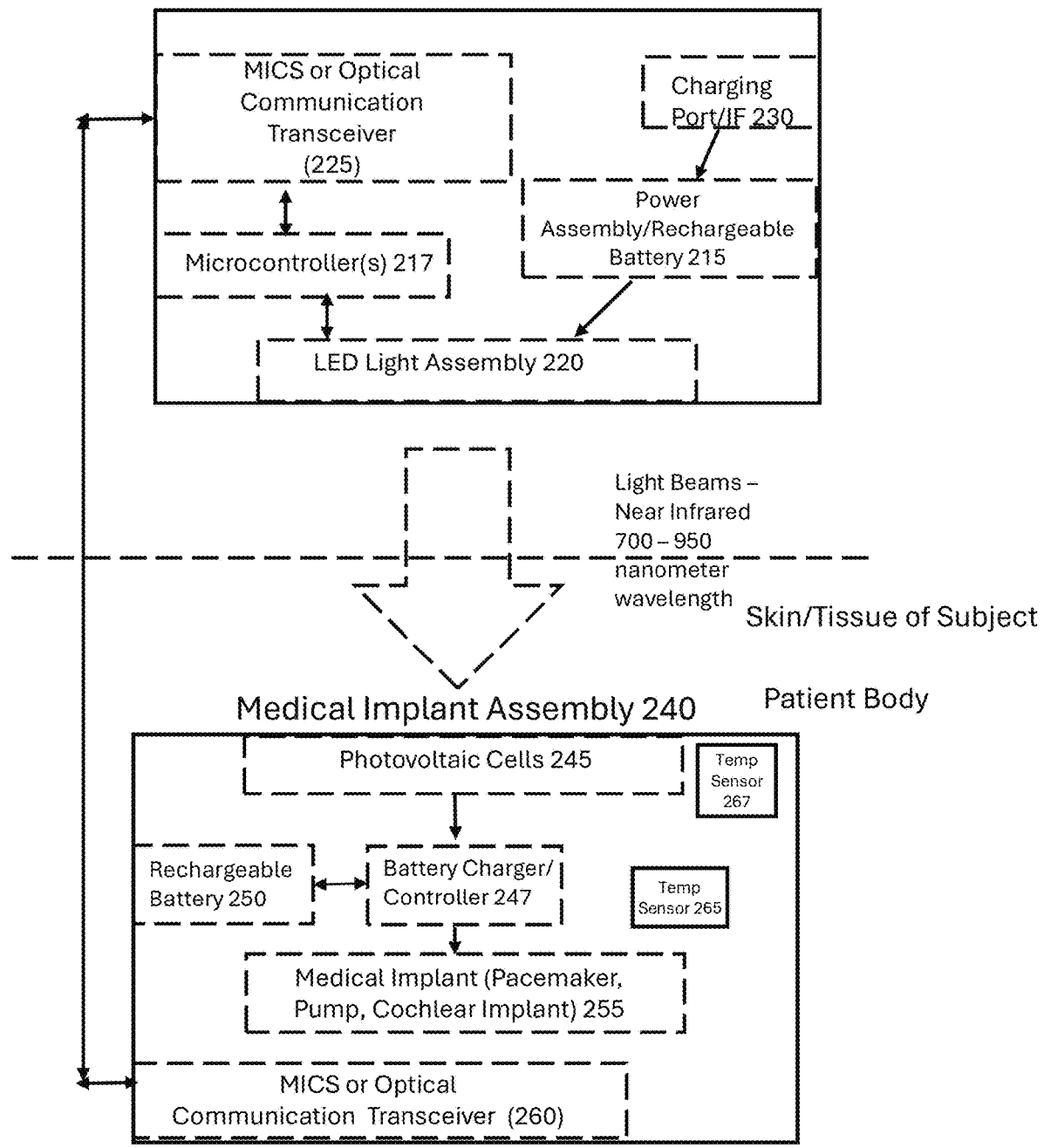

OPTICAL POWER DELIVERY TO IMPLANTED MEDICAL DEVICES

CROSS-REFERENCE TO RELATED APPLICATIONS/INCORPORATION BY REFERENCE

This application claims priority to U.S. provisional patent application Ser. No. 63/755,437, filed Feb. 7, 2025, entitled "Optical Power Delivery to Implanted Medical Devices," the disclosure of which is hereby incorporated by reference in its entirety.

FIELD OF TECHNOLOGY

The claimed subject matter and technology is related to a system and method to deliver optical wireless power to implantable medical devices.

BACKGROUND

Medical device implants perform important functions such as regulating heart rhythms with pacemakers, diabetes management with insulin pumps, restoration of hearing with cochlear implants, and other functions. While advances in electronics has opened up the potential for miniaturization, the battery size typically sets the lower limit to the size of the device. In theory, a smaller battery with RF wireless charging can solve this problem, however, the size of the RF antenna prevents further miniaturization.

BRIEF DESCRIPTION OF DRAWINGS

FIG. 2A is a block diagram that illustrates an optical wireless power delivery system to transmit optical power to an implantable medical device assembly through a subject's skin or tissue according to exemplary embodiments.

DETAILED DESCRIPTION OF THE DISCLOSURE

Figure 1:
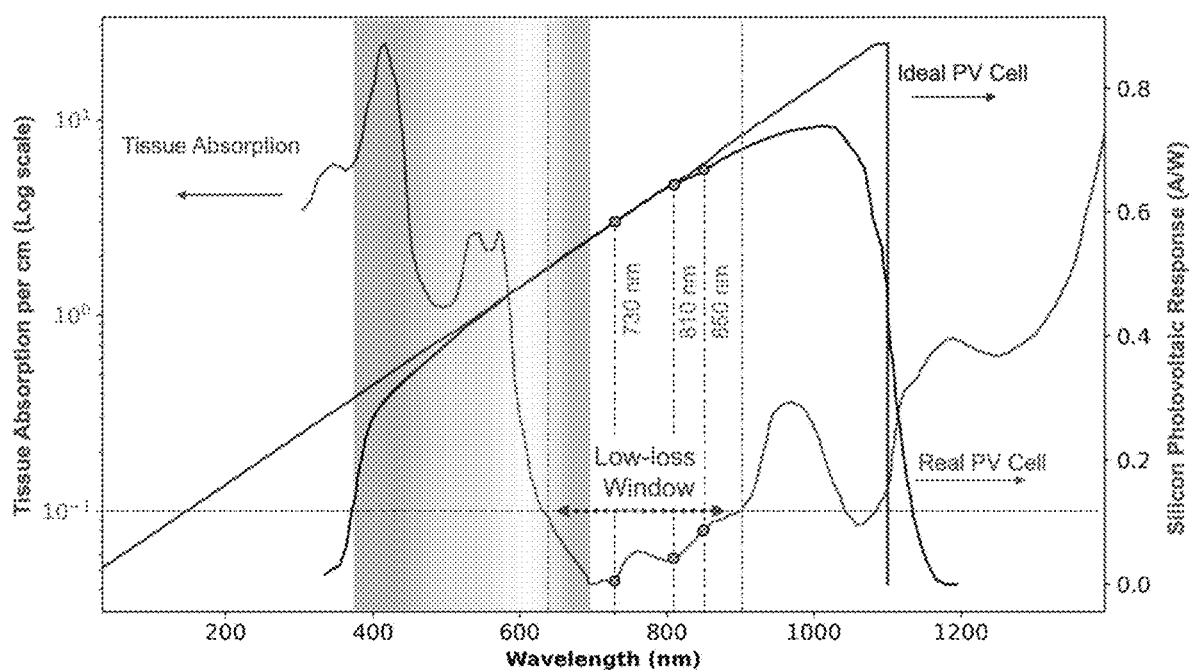
FIG. 1 illustrates a tissue absorption spectrum relative to the response of a silicon photovoltaic cell according to exemplary embodiments.

The following detailed description provides a better understanding of the features and advantages of the subject matter described in the present disclosure in accordance with the embodiments disclosed herein. In the following description, reference is made to the accompanying drawings, which form a part hereof, and in which is shown, by way of illustration, various embodiments of the present disclosure.

Optical power delivery to medical implants, proposed herein, can potentially solve the above-identified problem because it is not subject to antenna size limitation due to the much shorter wavelength of the optical power beam. The ability to charge the battery of the implantable medical device on a regular basis leads to a smaller battery size and potentially a less invasive implant. The technology described herein utilizes optical power delivery as a solution to power a smaller implant. The technology allows wireless energy transfer through tissue at the visible and near-infrared wavelength biological windows for optimal penetration. Medical implant device and implanted medical device may be utilized interchangeably throughout the specification.

The absorption properties of human tissue vary depending on tissue composition and optical wavelength. A primary component of human tissue is water which strongly absorbs light in the infrared (IR) range, particularly light beyond 1,300 nanometers (nm). On the other hand, minimal absorption occurs in the visible light spectrum, thus allowing light to penetrate human or subject tissue.

A second important molecule affecting tissue absorption is hemoglobin that is found in red blood cells and responsible for oxygen delivery to cells. Hemoglobin dominates the absorption in the visible range. Hemoglobin has specific absorption peaks around 415 nm, 540 nm, and 577 nm for oxygenated hemoglobin (HbO2) and at 430 nm and around 550 nm for deoxygenated hemoglobin (Hb). As a side note, blood oximeters utilize differential absorption of oxygenated and deoxygenated hemoglobin.

A third primary molecule is melanin. Melanin is responsible for a subject's skin pigment and acts as a ultraviolet light (UV) blocker protecting the subject's skin. Melanin has a broad and monotonic spectrum. Its absorption rate is high for UV light but absorbs the absorption rate decreases from the UV light spectrum to the near infrared (NIR) spectrum.

Finally, lipid is a common molecule that exist in various amounts in different part of the body. Lipids absorb light primarily in the mid-IR light range due to vibrational transitions of the C—H and C—O bonds. Lipids also have frequency overtones at shorter wavelengths in the near IR.

Accordingly, based on the molecules absorption rates discussed above, overall, there are two spectral ranges of interest for optical power delivery inside a subject's body (e.g., skin and/or tissue). In exemplary embodiments, the visible (400-700 nm) range light penetrates a subject's tissue by a modest amount, but this visible spectral range is limited due to absorption by hemoglobin and/or melanin molecules. In exemplary embodiments, a second range of interest is the 700-900 nm or near-IR spectral range, (also known as the biological window) where the absorption by the hemoglobin and water modules are both low enough to allow deeper penetration. The upper limit of this spectral light band is limited to about 900 nm in order to avoid the 980 nm water molecule peak. Not surprisingly, this window is used in optical coherence tomography (OCT) and photodynamic therapy and near IR spectroscopy. Shorter wavelengths (100-400 nm) are generally avoided due to high absorption of melanin and hemoglobin, but also because the high photon energy can cause photochemical damage to the tissue.

FIG. 1 illustrates a tissue absorption spectrum relative to the response of a silicon photovoltaic cell according to exemplary embodiments. As shown in FIG. 1, based on the tissue absorption spectrum and the efficiency of silicon photovoltaic cells (discussed later), the optimum optical wavelength band for the subject matters is 700-900 nm. The 3 wavelengths shown are for the LED light assemblies used in the power delivery experiments that are described below. The LED light assemblies may also be referred to as a plurality of LED lights in this application.

One of the measurement techniques that has been successful for characterizing the optical absorption in tissue is a diffusive time domain spectroscopy. Here, a narrow pulse of light (<100 picoseconds) is injected into the medium. The injected photons undergo multiple scattering and absorption events and the scattered photons are then collected at a certain distance from the source and the photon arrival times are recorded. The photon arrival times are converted into the histogram of a distribution of time-of-flight of photons or temporal point spread function. This distribution is delayed, attenuated and broadened with respect to the injected pulse. Higher scattering leads to a more delayed and a broader distribution and higher absorption reduces the amplitude and changes the slope of the tail of the distribution. Since light absorption and scattering have different effects on the distribution, they can be extracted independently while using a single source-detector separation.

Energy conversion efficiency of silicon photovoltaic cell—While the theoretical efficiency of silicon photovoltaic cell is limited to about 33% as described by the Shockley-Queisser limit, this limit is for a broadband radiation spectrum of the sun. Photovoltaic cells can achieve much higher efficiencies for the narrowband laser light or near-infrared light when the laser or near-infrared wavelength is matched to the semiconductor bandgap. Energy conversion efficiencies well greater than 50% can have been reported for multi-junction GaAs converters.

FIG. 1 shows the responsivity of silicon photovoltaic cells vs. wavelength for the visible and near IR wavelengths that match the low attenuation window of hemoglobin and water. Responsivity greater than 0.5 A/W can be achieved in the 700-1000 nm range which well overlaps with the transparency window of the tissue (e.g., the ability to use light beams in the 700-1000 nm range). These were achieved in testing.

Maximum Permissible Exposure (MPE)—The Maximum Permissible (light) Exposure (MPE) depends wavelengths and is subject to safety guidelines provided by organizations such as the International Commission on Non-Ionizing Radiation Protection (ICNIRP), the American National Standards Institute (ANSI), and the IEC 60825 standard. These limits are designed to prevent thermal and photochemical damage. According to the ANSI Z136.1, the MPE in the IR-A (700-1400 nm) band is 100 mW/cm$^2$ for durations of a few seconds for laser light. The MPE for LED light is typically higher than that for laser light of comparable wavelength and power.

Battery Capacity-Considering a pacemaker as an example, the device battery has an energy capacity of approximately 2500 mWh (mWatt-Hour) and lasts for approximately 10 years. This translates into a 125 mAh capacity for a battery that needs to be charged every 6 months.

Experiments-Experimental results are shown in Tables 1 and 2. The experiments consisted of using LED arrays at wavelengths of 730 nm, 810 nm and 850 nm calibrated to provide a safe illumination intensity of 100 mW/cm$^2$ (sunlight intensity). The energy delivery to a silicon solar cell placed beneath a 10 mm thick tissue sample (e.g., was measured and used to estimate the charging time for the battery capacity of 4.8 mWh (e.g., one week of charging shown in Table 1) versus 125 mWh (six months of charging as shown in Table 2)). The results in Table 1 illustrate charging parameters needed for 1 week of charge (e.g., 4.8 mWh). The results in Table 2 show that even at a low intensity of 100 mW/cm$^2$, the battery can be charged in less than 30 minutes. For a pacemaker in Table 2, this charging process would be repeated every 6 months. The 810 nm wavelength produced the best result among the three wavelengths. We note the IR LEDs used here lack any visible or UV radiation. Accordingly, a higher exposure level than sunlight may be possible further reducing the charging time of the battery in the pacemaker or medical implant device. Tables 1 and 2 below illustrates charging time based on wavelength according to exemplary embodiments. As is illustrated below there appears to be peak efficiency close to 810 nm wavelength in the spectrum of light.

TABLE 1

| Wavelength | 530 nm | 730 nm | 810 nm | 850 nm |
|---|---|---|---|---|
| No Sample | 458 mW | 600 mW | 720 mW | 737 mW |
| 10 mm thick meat | 0.60 mW | 184.3 mW | 259 mW | 211 mW |
| Time for 4.8 mWh | 480 min. | 1.6 min. | 1.2 min. | 1.4 min. |

TABLE 2

| Wavelength | 730 nm | 810 nm | 850 nm |
|---|---|---|---|
| No Sample | 600 mW | 720 mW | 737 mW |
| 10 mm thick meat | 184.3 mW | 259 mW | 211 mW |
| Time for 125 mWh | 40.8 min. | 29 min. | 35.6 min. |

Other wavelengths of light may be utilized to charge the silicon photovoltaic cells in the medical implant devices such as laser devices emitting laser light beams having 400 to 1000 nm range, although 700 to 900 nm provides optimal charging. In addition, other sources of light, such as mobile device lighting assemblies (accessed via flashlight function) may also be utilized to charge the silicon photovoltaic cells in the medical implant devices. In some implementations, this may allow for emergency or quick charging of the photovoltaic cells in the medical implant devices when power is low and a normal charging device is not available but the medical implant device may need to be charged. This may also be known as topping off a charge.

Optical power delivery may allow users to minimize medical implant device size by overcoming battery and RF antenna limitations. Using near-infrared light (700-900 nm), which aligns with low tissue absorption and high silicon photovoltaic efficiency, light or optical charging of the medical implant device is shown. An important feature of the light or optical charging system and method described herein of medical implant device may eliminate the need for surgical replacement of the battery.

FIG. 2A is a block diagram that illustrates an optical wireless power delivery system to transmit optical power to an implantable medical device assembly through a subject's skin or tissue according to exemplary embodiments. In other words, the charging assembly 210 (or flexible adhesive package 210) may be optically coupled to the medical implant assembly and may transmit light beams through a patient or subject's skin or tissue. In exemplary embodiments, the optical wireless power delivery system 200 may include a charging assembly 210 (which in some embodiments, may include a flexible adhesive package or be integrated into a flexible adhesive package) and a medical implant assembly 240. In exemplary embodiments, the charging assembly or flexible adhesive package 210 may be placed on the patient's skin over the medical implant assembly 240 (and/or specifically the one or more photovoltaic cells 245 of the medical implant assembly) to charge the rechargeable battery 250 in the medical implant assembly 240). In some embodiments, the flexible adhesive package may be adhered to the patient's skin. In some embodiments, the flexible adhesive package or charging assembly 210 may include a clear or more transparent opening to allow better emission of the one or more LED light assemblies towards the patient's skin and/or tissue. The flexible adhesive package may be made of medical patches using adhesives made by 3M. The packaging may include the components of the charging assembly. The packaging may be flexible to conform with the patient's body. The flexible packaging may be made of natural rubber, synthetic rubber, plastic and/or vinyl or similar circumstances. In exemplary embodiments, the flexible packaging may have an adhesive on one side of the flexible packaging. This side may be adhered to the subject's skin so that the charging assembly does not move during charging. The flexible adhesive package may also be referred to as a flexible electronics package or pack which includes one or more adhesive sides (which may or may not be pull-off adhesives). Inside the flexible adhesive package or charging assembly 210 may be flexible electronic circuit boards which includes the components discussed above with respect to FIG. 2A, e.g., charging ports or interfaces, one or more power supplies, one or more microcontrollers, one or more MICS wireless transceivers (or optical transceivers), and or one or more LED light assemblies (or laser light assemblies). In some embodiment, the flexible adhesive package 210 and/or the flexible circuit board may include rechargeable batteries although these may be separate components that are coupled to or connected to by the flexible circuit board (either in the flexible adhesive package or flexible electronics package or exterior to these packages). A flexible circuit board (also known as a flex PCB) is an electronic circuit made on a flexible substrate, typically composed of materials like polyimide or polyester. Flexible circuit boards may bend, twist, and fold without losing functionality. They are widely used in applications where space is limited, and flexibility is essential, such as in wearable devices, mobile phones, or medical equipment.

In exemplary embodiments, the portable charging assembly (or flexible adhesive package) 210 may include one or more Medical Implant Communication System (MICS) wireless transceivers 225, one or more charging ports or Interfaces 230, one or more rechargeable power supplies or assemblies 215, one or more microcontrollers 217, and/or one or more LED light assemblies 220. In exemplary embodiments, the medical implant assembly 240 may include one or more photovoltaic cells 245 (which may be referred to as a photovoltaic assembly), one or more battery charging circuits or controllers 247, one or more rechargeable batteries 250, one or medical implant devices 255, one or more temperature sensors 265 267, and/or one or more MICS wireless communication transceivers 260. In some embodiments, the medical implant assembly may also include one or more processors or controllers (not shown). In other embodiments, the battery charge controllers 247 may include the controller or processor. Alternatively, there may be some embodiments, the medical implant assembly 240 may include the microcontroller or processor. In other embodiments, the charging assembly or flexible adhesive package 210 may include one or more microcontrollers 217 which may control operations of the MICS wireless communication transceivers 225 and/or the LED light assemblies 220. In these embodiments, the one or more microcontrollers 217 may receive power from the one or more power assemblies or rechargeable batteries 215. The one or more microcontrollers 217 may also control other components of the charging assembly or flexible adhesive package 210.

In exemplary embodiments, an external power source may generate electrical power and may transfer the electrical power via a cable to the charging port or interface 205 on the charging assembly 210. In exemplary embodiments, the cable and/or charging port or interface may utilize a Universal Serial Bus-C (USB-C) interface, a USB-A interface, a USB-B interface or other power and/or data transfer protocols.

In exemplary embodiments, the power assembly 215 may include one or more rechargeable batteries 215. In exemplary embodiments, the charging port or interface 230 may be electrically coupled or connected to the one or more rechargeable batteries 215 and may charge the one or more rechargeable batteries 215. In exemplary embodiments, the one or more rechargeable batteries 215 may provide power to components of the charging assembly or flexible adhesive packages 210, such as the MICS wireless transceiver 225 and/or the one or more LED light assemblies 220 (and/or the one or more microcontrollers 217). In exemplary embodiments, the one or more microcontrollers 217 may control operations of the MICS wireless communication transceiver 225, the power assembly or rechargeable battery(s) 215 and/or the one or more LED light assemblies 220. In addition, other wireless communication transceivers may also be utilized to communicate between the charging assembly 210 and/or the medical implant assembly 240 (and/or other computing devices).

Figure 3A:
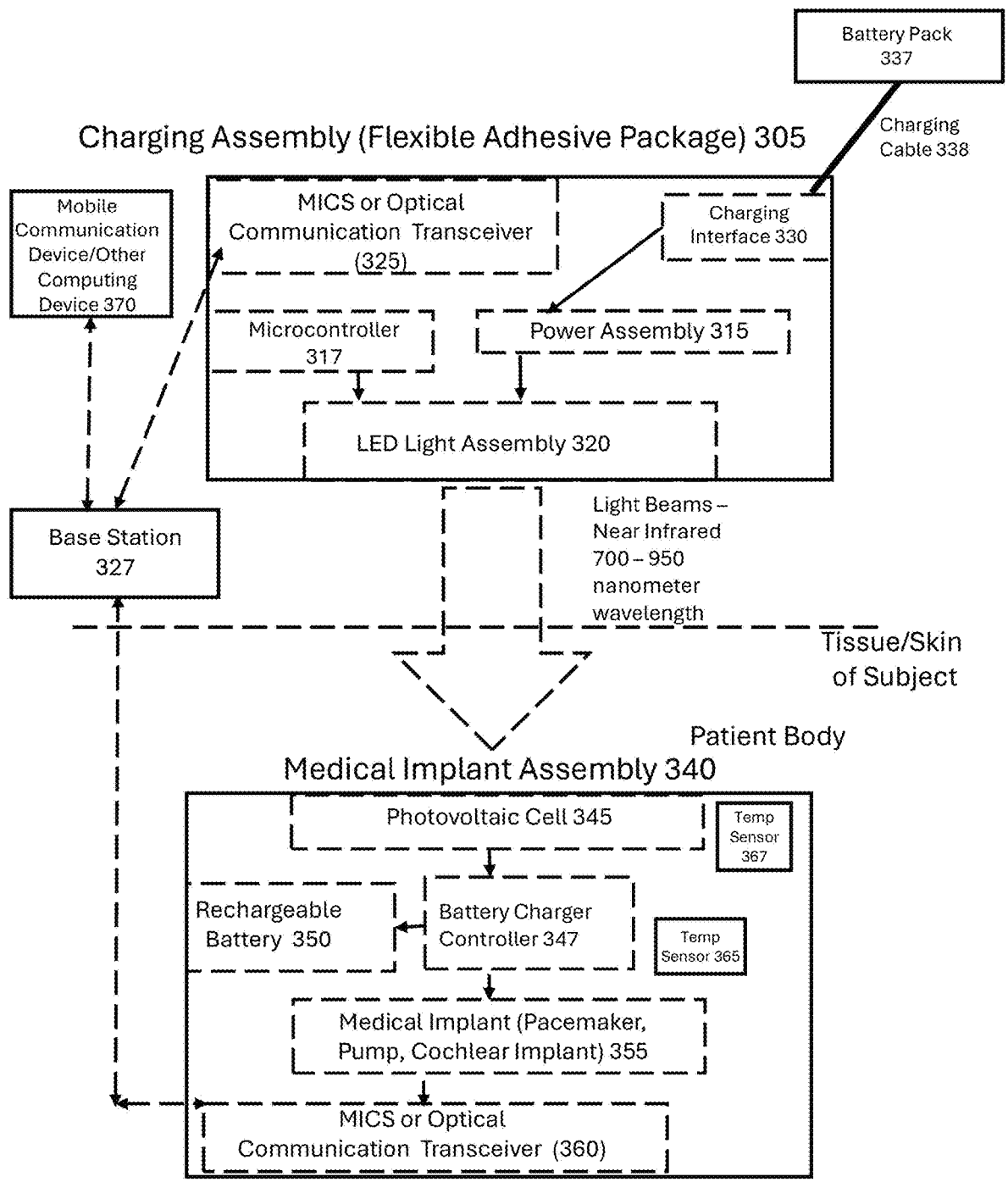
FIG. 3A illustrates a wireless optical power system for providing power to a medical implant assembly according to another exemplary embodiment.
Figure 3B:
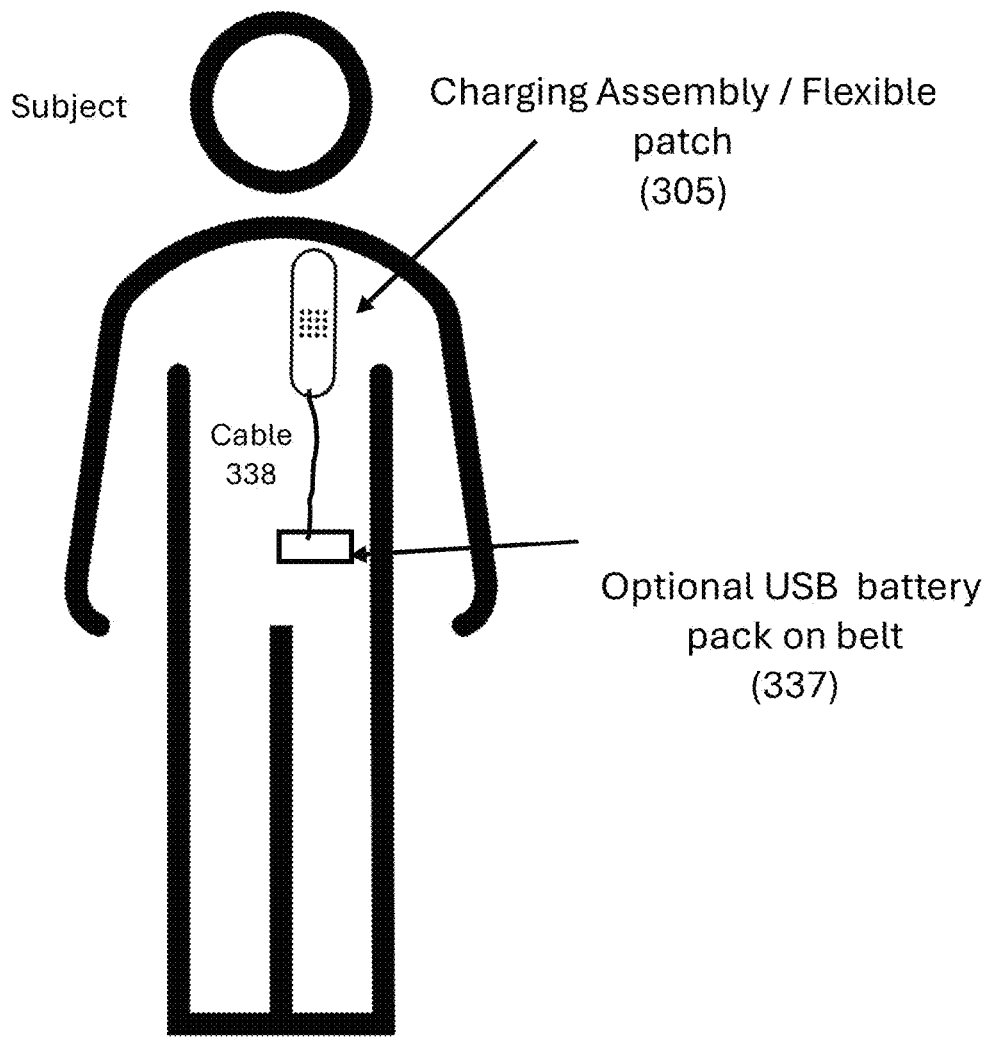
FIG. 3B illustrates a location of a separated charging assembly and battery pack according to exemplary embodiments.
Figure 3C:
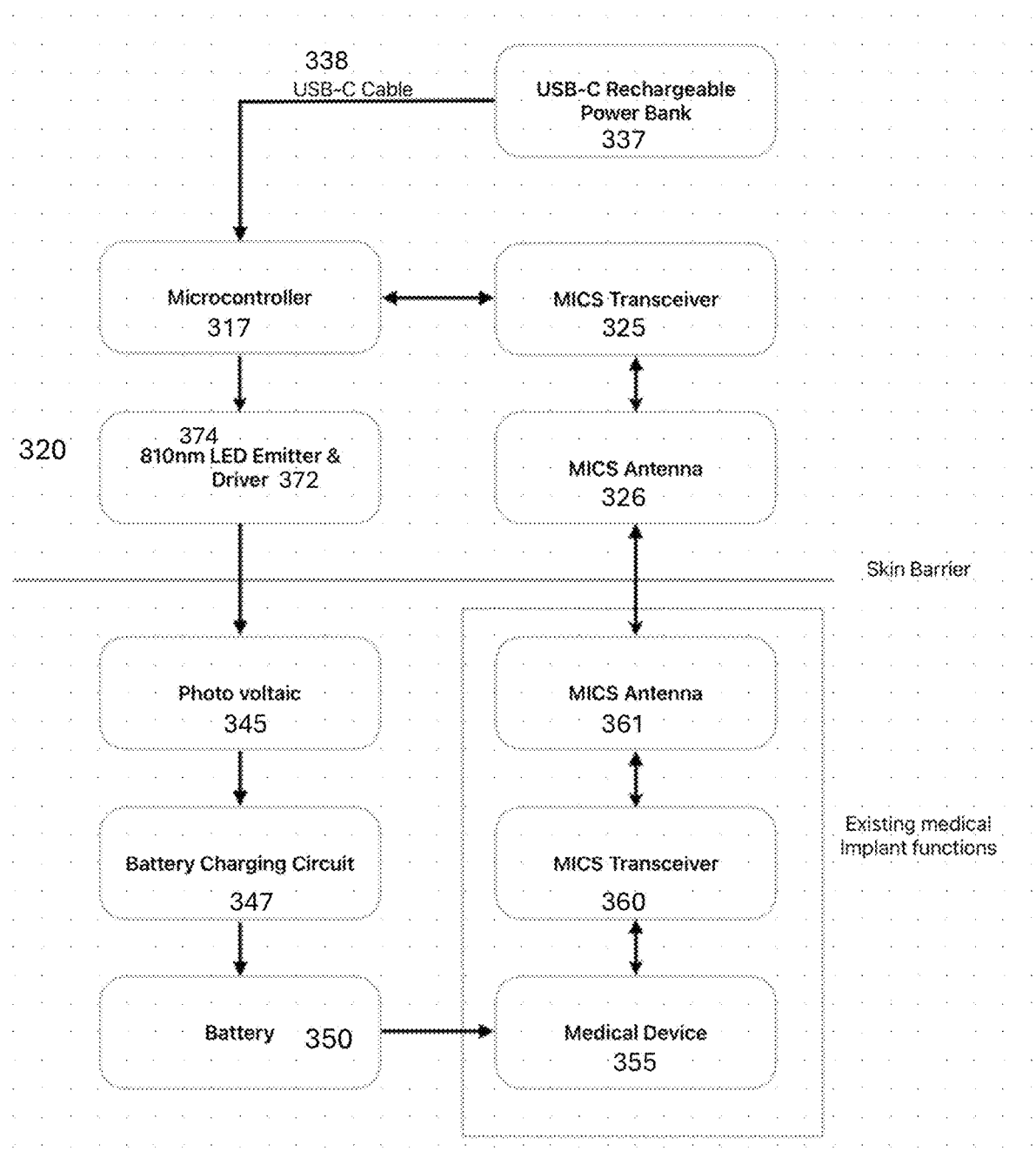
FIG. 3C illustrates a block diagram of a wireless optical power system for providing power to a medical implant assembly according to another exemplary embodiment.

In exemplary embodiments, the one or more LED light assemblies 220 may include an LED driver 272 and/or one or more LED lights 274 (as shown in FIG. 3C). FIG. 3C illustrates a block diagram of a wireless optical power system for providing power to a medical implant assembly according to another exemplary embodiment. In exemplary embodiments, the one or more rechargeable batteries 215 may be coupled to the LED light assemblies 220. In some embodiments, the one or more microcontrollers 217 may be connected or coupled to the LED light assemblies 220 (e.g., connected and/or coupled to the LED driver 272 which controls operations and parameters of the one or more LED lights 274). In exemplary embodiments, the LED light assemblies 220 (e.g., the one or more LED lights 274) may emit light with a wavelength of 810 nanometers. In other embodiments, the LED light assemblies 220 may emit light beams with a wavelength having a range from 730 nanometers to 850 nanometers. In exemplary embodiments, the LED light assemblies 220 (e.g., the one or more LED lights 274) may emit light beams with wavelengths ranging from 700 nm to 900 nm. These wavelengths have been shown to have optimal charging capabilities through the skin and/or tissue for medical implant assembly's battery 250. However, other light wavelengths of the LED light assemblies 220 work in charging the medical implant assembly 240 (such as light beams having wavelengths ranging from 400 nm to 700 nm (or laser light beam having similar wavelengths).

Figure 2B:
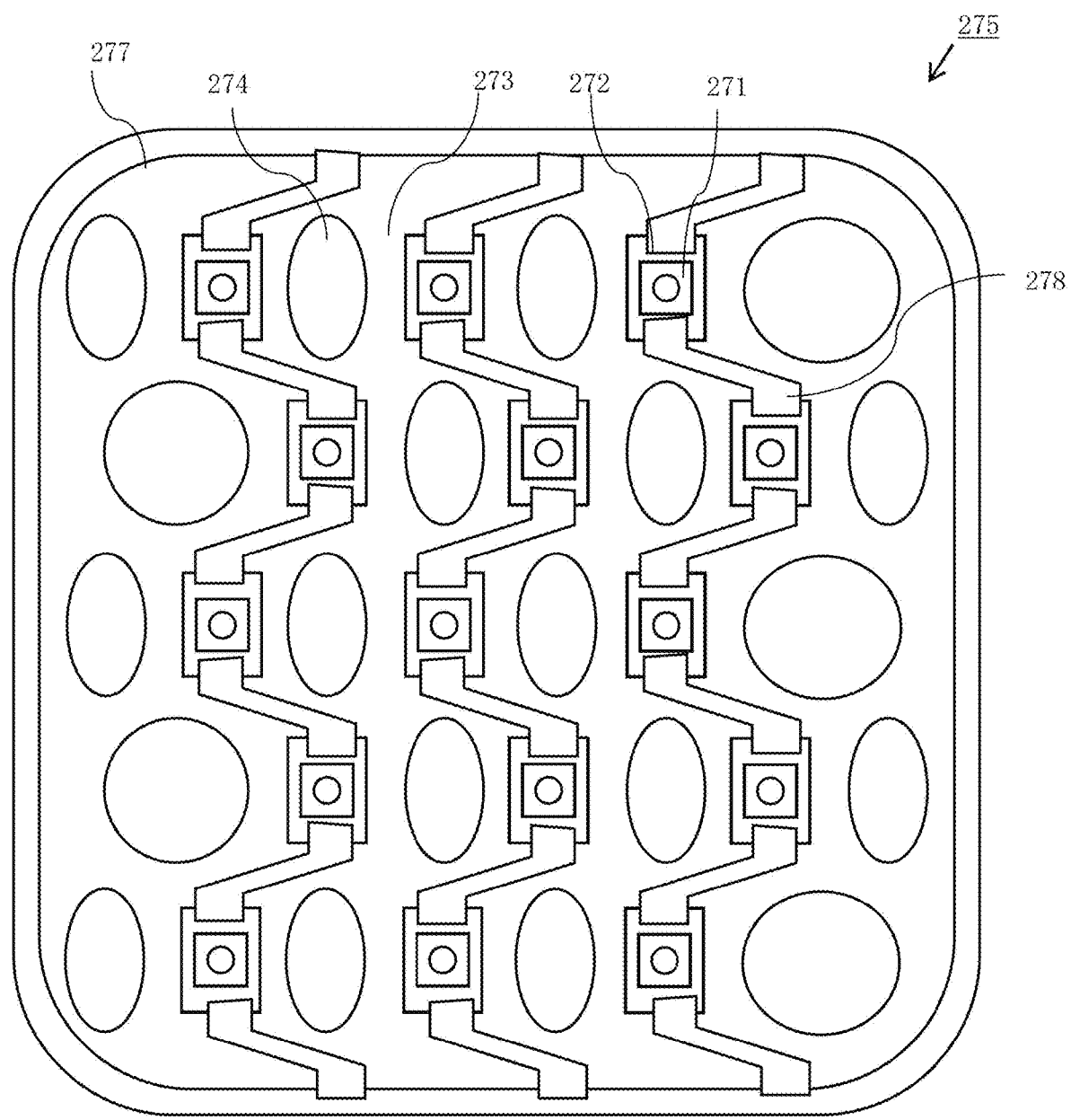
FIG. 2B illustrates a specific embodiments of LED light assemblies according to exemplary embodiments.
Figure 2C:
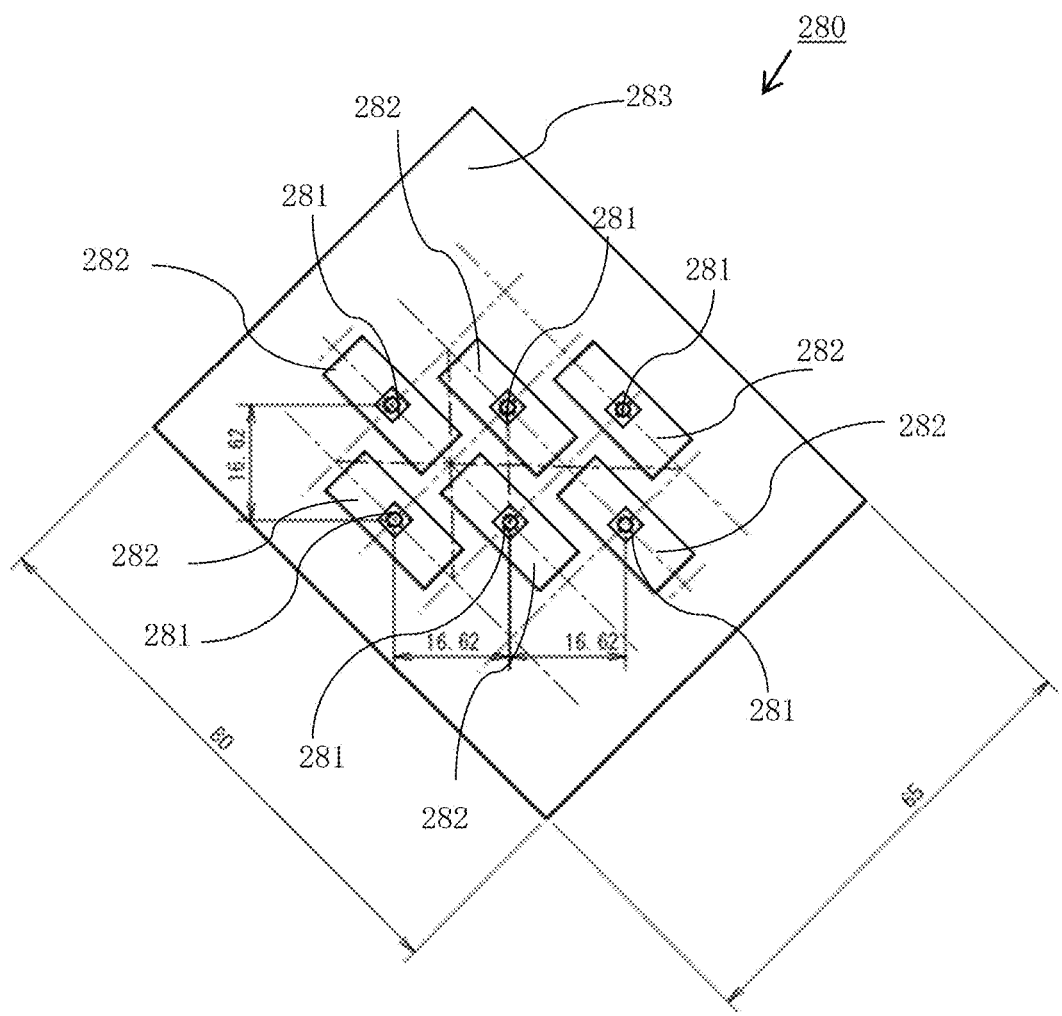
FIG. 2C illustrates another specific embodiment of LED light assemblies according to exemplary embodiments.

In exemplary embodiments, there may be one LED light in the LED light assemblies 220. In other embodiments, there may be six LED lights in one or more LED light assemblies 220. In exemplary embodiments, the number of LED lights 274 in the LED light assembly 220 may range from 1 to 20 LED lights. In other embodiments, the light assembly may be a laser light beam having similar wavelengths to those discussed above (e.g., light beams or a laser light beam having wavelengths ranging from 700 nm to 900 nm or. FIGS. 2B and 2C illustrate LED light assemblies with 15 LEDs lights and 6 LED lights, respectively.

In FIG. 2B, the LED light assembly 220 may include a light shield 217 to prevent light from being directed away from the LED light assembly 220. In exemplary embodiments, in FIG. 2B, the LED light assembly 220 or 275 may include a printed circuit board, a light shield 277, a hole 274, a LED base plate 273, a LED mount base 272, and/or a LED light 271. In FIG. 2B, there may be 15 LED lights mounted on 15 LED mount bases. In FIG. 2C, the LED base plate 283 may include six LED mount bases 282 and/or six LED lights 281.

In exemplary embodiments, the MICS wireless transceiver 225 may communicate with the MICS wireless transceiver 260 in the medical implant assembly 240 and/or with a base station (which will be described in FIG. 3A later). In exemplary embodiments, the MICS wireless transceiver 260 may communicate a battery status or charging parameter to the charging assembly 210 (or flexible adhesive package) so that the charging assembly 210 knows to terminate or deactivate the LED light assemblies 220. In these embodiments, the one or more microcontrollers 217 may receive the battery status or charging parameters from the MICS transceiver 225 and send a command or message to the LED light assemblies 220 in response. In exemplary embodiments, the MICS wireless transceivers 225 or 260 may be a Microchip Technologies ZL70103 MICS radiofrequency transceiver. In exemplary embodiments, the MICS wireless transceivers 225 or 260 may each include a RF antenna to transmit communications. In some embodiments, the RF antenna may be incorporated into a chip containing the MICS transceiver while in other embodiments, the MICS transceiver and MICS antenna may be on separate physical devices or may be separated logically. In exemplary embodiments, the MICS transceiver and/or MICS antenna may be replaced with optical bidirectional transceiver(s) to transmit parameters between the charging assembly 210 and/or the medical implant assembly 240. This would also require that the medical implant assembly 240 include a LED light assembly (or multiple LED lights) and/or the charging assembly 210 may include a photovoltaic assembly (or multiple photovoltaic cells or arrays).

In exemplary embodiments, the transmitted light beams from the LED light assemblies 220 may be near infrared light beams which may have between a 700 to 950 nanometer wavelength. In exemplary embodiments, the transmitted LED light beams may be transmitted through a patient's skin and/or tissue to the medical implant assembly 240. In exemplary embodiments, the medical implant assembly 240 may be located under approximately 10 mm of tissue. In other embodiments, the medical implant assembly 240 may be located under tissue ranging from 1 mm of tissue to 20 mm of tissue. This allows the LED light beams to pass through the tissue and scatter in a uniform fashion to be received uniformly by the one or more photovoltaic cells 245. Similarly, but less optimally, the transmitted light beams from the LED light assemblies 220 may be near visible light beams which may have between a 400 to 700 nanometer wavelength In exemplary embodiments, a charging assembly may include one or more LED light assemblies configured to transmit a plurality of light beams to a skin of the subject; a rechargeable power supply configured to provide power to the charging assembly; a charging port (e.g., USB-C port or AC adapter) electronically coupled to the rechargeable power supply to receive external power to charge the rechargeable power supply; and a first Medical Implant Communication System wireless transceiver configured to communicate with the implant device and/or a base station to provide status of a rechargeable power supply in the medical implant assembly. In these embodiments, the microcontroller 217 may control operations of the charging assembly 220 or flexible adhesive package. In these embodiments, the charging assembly may be integrated into a flexible adhesive patch that may be attached to the subject's skin. In exemplary embodiments, the plurality of light beams may have a near infrared wavelength ranging from 700 to 950 nanometers (nm).

In exemplary embodiments, the one or more photovoltaic cells 245 may receive the plurality of LED light beams that have been transmitted through the subject's skin and/or tissue. In exemplary embodiments, the one or more photovoltaic cells 245 may convert the plurality of LED light beams into electrical energy. The one or more photovoltaic cells 245 may also be referred to as a photovoltaic assembly or a photovoltaic array. In some embodiments, in order to increase the efficiency of the conversion at the near infrared wavelength of the photovoltaic cells, the one or more photovoltaic cells 245 may include a coating to allow easier transmission of light at the wavelengths identified above. In exemplary embodiments, the one or more photovoltaic cells may include a surface optical coating on the one or more photovoltaic cells, the surface optical coating configured to minimize a reflection of the plurality of light beams.

In exemplary embodiments, the one or more photovoltaic cells 245 may be coupled or connected to the battery charge controller or circuits 247. In exemplary embodiments, the one or more photovoltaic cells 245 may transfer the electrical power to the battery charge controller or circuits 247. In exemplary embodiments, the battery charge controller or circuits 247 may be coupled or connected to the rechargeable battery 250 in the medical implant assembly 240. In exemplary embodiments, the battery charge controller or circuits 247 may utilize the electrical power to charge the rechargeable battery 250 of the medical implant device 255. In exemplary embodiments, the battery charge controller or circuits 247 may monitor a charging status or parameter of the rechargeable battery 250. In exemplary embodiments, the battery charge controller or circuits 247 and/or rechargeable battery 250 may provide power to components of the medical implant assembly 240 including but not limited to the medical implant device 255, the MICS wireless transceiver 260 and/or temperature sensors 265 or 267 in the medical implant assembly 240.

In exemplary embodiments, the medical implant device 250 may receive the electrical power from the battery charge controller or circuits 247 and/or rechargeable battery 250 and may perform functions to assist the user with the condition or disease the uses is dealing with by having the medical implant device 250. For example, the medical implant device may be a pacemaker and may monitor heart conditions and parameters and provide electrical pulses to a subject's heart, whereas with an insulin pump/monitor, the insulin monitor may monitor blood glucose levels and provide insulin as necessary. In exemplary embodiments, the medical implant device 250 may generate physiological parameters, device conditions, and/or other parameters with respect to the patient or subject. These parameters may include real-time heart health data from a pacemaker implant, audio processing information from a cochlear implant, stimulation parameters and neurological parameters for a deep brain stimulator, glucose and related measurements and insulin delivery measurements for implanted glucose monitors and insulin pumps, and control and position information for prosthetic limbs or joints. These parameters may be utilized by software applications on the base station 327 and/or the mobile communication device (or other computing devices) 370 (both shown in FIG. 3A discussed below).

In exemplary embodiments, the medical implant device 250 may be connected and/or coupled to the MICS wireless transceiver 260. In exemplary embodiments, the medical implant device 250 may utilize the MICS wireless transceiver 260 to transmit the physiological parameters, device conditions and/or other parameters to the MICS communication transceiver 225 in the charging assembly 210 and/or to an external MICS base station (not shown in FIG. 2A). In exemplary embodiments, the rechargeable battery 250 and/or the battery charge controller 247 may utilize the MICS wireless transceiver 260 to transmit the battery charge parameters or status to the MICS wireless transceiver 225 in the charging assembly 210 to assist in controlling activation/deactivation of the LED light assemblies 220 (the battery charge parameters or status may also be transmitted to the charging assembly through the base station). In exemplary embodiments, the charging assembly or flexible adhesive package 210 may not utilize the physiological parameters, device conditions and/or other parameters from the medical implant device because the charging assembly or flexible adhesive package 210 is focused on charging the rechargeable battery 250 in the medical implant assembly 240 and medical implant device 255. In exemplary embodiments, an optical bidirectional data transceiver may be utilized in both the charging assembly 210 and/or the medical implant assembly 240 in place of the MICS wireless transceiver 260.

In exemplary embodiments, the medical implant assembly 240 may include the medical implant device 255, which may be a pacemaker, cochlear ear implants, blood glucose/insulin pump or monitor, deep brain stimulators and/or an implanted artificial joint implanted in the subject; a rechargeable power supply or rechargeable battery 250 configured to provide power to the medical device and other components of the medical implant assembly; a battery charger circuit or controller 247 configured to charge the rechargeable battery or rechargeable power supply; a photovoltaic assembly 245 (or a plurality of photovoltaic cells) configured to convert the plurality of light beams transmitted by the one or more LED devices 220 to electrical power to charge the rechargeable battery 250; and a MICS wireless transceiver 260 configured to communicate status parameters of the medical implant assembly 240. In exemplary embodiments, one or more temperature sensors 265 and 267 may monitor temperature in the medical implant assembly 240. In exemplary embodiments, one of the temperature sensors 265 may monitor temperature of the skin or tissue of the patient, the rechargeable battery 250, the battery charger controller 247 and/or the medical implant device 255. If a temperature is above a threshold level, the temperature sensor 265 and/or the battery charger controller 247 may communicate commands or instructions to the MICS wireless transceiver 260 in order to communicate the commands or instructions to the MICS wireless transceiver 225 in the charging assembly 210 in order to deactivate the one or more LED light assemblies 220 (via the microcontroller 217). In exemplary embodiments, the temperature sensor 267 may monitor temperatures of the one or more photovoltaic cells 245 and/or tissue around the cells in order to determine if too much heat is being generated. As discussed above, if the temperature is above a threshold level, the temperature sensor 267 and/or the battery charger controller 247 may communicate commands or instructions to the MICS wireless transceiver 260 in order to communicate the commands or instructions to the MICS wireless transceiver 225 in the charging assembly 210 in order to deactivate the one or more LED light assemblies 220 (via the microcontroller 217). In exemplary embodiments, the temperature sensors 265 and 267 may also communicate with components of the medical implant assembly 240 to turn off or deactivate these components to minimize heat in the components. In exemplary embodiments, the one or more photovoltaic cells, the photovoltaic array or the photovoltaic assembly may be multi-junction photovoltaic cells. In these embodiments, the multi-junction photovoltaic cells may be GaAs photovoltaic cells that have approximately an 800 nanometer band light source.

In exemplary embodiments, the charging assembly 220 may charge the rechargeable battery 250 in the medical implant assembly when the rechargeable battery 250 is almost out of charge. However, in other embodiments, because the medical implant assembly 240 is so vital to the subject's wellbeing, it may be better to recharge the rechargeable battery 250 once the charging level in the rechargeable battery 250 has passed a charging value low level threshold. In exemplary embodiments, the charging value threshold may be 25 percent, which means that the rechargeable battery 250 has less than 25 percent charge left is when it should be recharged. Thus, in these embodiments, the charging assembly 210 may charge the rechargeable battery 250 in the medical implant assembly 240 utilizing the one or more LED assemblies 220 when the charging value threshold is less than 25 percent. In other cases, the charging assembly 210 may charge the rechargeable battery 250 in the medical implant assembly 240 utilize the one or more LED assemblies 220 on a periodic basis (e.g., every two weeks or every month) in order to top off the charge of the rechargeable battery 250 in the medical implant assembly 240. This is better for rechargeable battery health and make may the patient feel safer if they know that the rechargeable battery may be charged once it reaches a certain level.

FIG. 3A illustrates a wireless optical power system for providing power to a medical implant assembly according to another exemplary embodiment. FIG. 3A is different from FIG. 2A in that the battery pack or rechargeable battery is not part of the charging assembly or flexible adhesive package 310. In addition, FIG. 3A illustrates a MICS base station 327 to which the MICS wireless communication transceivers 360 or 325 may communicate rechargeable battery status parameters, subject parameters or measurements, and/or medical implant parameters or status indicators. Further, FIG. 3A illustrates a mobile communication device or other computing device 370 that the base station 327 can communicate battery status or parameters, subject or patient parameters or measurements and/or medical implant device or assembly parameters or status indicators. In exemplary embodiments, the base station 327 may communicate the medical implant parameters or status parameters or subject parameters to a mobile communication device and/or other computing device for processing by health-related software applications (or other applications requesting these parameters).

In exemplary embodiments, an external battery pack 337 may provide electrical power to the charging assembly or flexible adhesive package 305. In these embodiments, the external battery pack 337 may be external and/or separate from the charging assembly 310. This allows the charging assembly or flexible adhesive package 310 to be lighter on the subject's body so the subject does not have to worry about it falling off during charging. This also decreases the weight of the charging assembly or flexible adhesive package 305, which makes it easier for the flexible adhesive package 305 to stay adhered to the patient's skin. In some embodiments, as is illustrated in FIG. 3B, the battery pack 337 may be located or positioned on a subject's belt or waist. FIG. 3B illustrates a location of a separated charging assembly and battery pack according to exemplary embodiments. In these embodiments, the battery pack 337 may be coupled or connected to the charging assembly 305 via a cable 338, which may transfer the electrical power to the charging assembly or flexible adhesive package 305. In the charging assembly 305, the cable 338 may be coupled to a power interface 330. In exemplary embodiments, the power interface 330 may be coupled or connected to a power assembly (or power supply) 315. In some embodiments, the battery pack 337 may include a USB-C or other USB communication protocol charging battery. In some embodiments, the battery pack 337 may be a standard battery pack that can be purchased for other medical devices or electrical components. By moving the battery pack 337 away from the charging assembly or flexible adhesive package 320, the weight of the charging assembly 305 may be minimized and this may allow the charging assembly 305 to be more easily attached to the subject's body. The subject may be a human patient. The subject may also be an animal that has skin similar to human skin or that can be penetrated by optical light.

In these embodiments, the power supply 315 may provide power for the components and/or systems of the charging assembly (or flexible adhesive package) 305. These components may include the one or more microcontrollers 317, the one or more MICS wireless transceivers 325, and/or the one or more LED light assemblies 320, although other components may also receive power. In exemplary embodiments, the one or more microcontrollers 317 may control operations of the charging assembly 305 and specifically may control operations of the one or more LED light assemblies 320 and/or the MICS wireless transceivers 325. The operations of the charging assembly 305 are similar to those discussed above with respect to the charging assembly 210 in FIGS. 2A, 2B and 2C and are not repeated here and the method and systems discussed apply with equal force to these figures.

In FIG. 3A, in illustrative embodiments, the medical implant assembly 340 may operate in the same fashion as described in FIGS. 2A, 2B and 2C and will not be repeated here. The methods and systems described in FIGS. 2A, 2B and 2C can be utilized with FIGS. 3A, 3B and 3C. In FIG. 3A, the MICS wireless transceiver 360 may communicate generate physiological parameters, device conditions, and/or other parameters with respect to the patient or subject as well as battery status parameters to the MICS base station 327. In exemplary embodiments, the MICS base station 327 may already be used by the patient or subject to receive medical implant device parameters. In exemplary embodiments, the MICS base station 327 may communicate the battery status parameters to the charging assembly or flexible adhesive package 305 so that the charging assembly (e.g., the microcontroller 317) knows when to stop activating the LED light assemblies to charge the medical implant assembly 340. In exemplary embodiments, the MICS base station 327 may communicate the physiological parameters, device parameters and conditions and other parameters to the mobile computing device or other computing device 370. In exemplary embodiments, medical implant software may be stored on the mobile computing device or other computing device 370 may analyze the physiological parameters, device parameters and conditions and other parameters to determine next steps for the subject or patient, or how the medical implant device is operating.

FIG. 3C illustrates a block diagram of a wireless optical power system for providing power to a medical implant assembly according to another exemplary embodiment. In FIG. 3C, a USB-C rechargeable power bank or battery 337 may be coupled and/or connected to a microcontroller 317 in a charging assembly or flexible adhesive package. In exemplary embodiments, the microcontroller is coupled and/or connected to the MICS wireless transceiver 325 and/or the LED assembly (or plurality of LED lights) 320. The LED assembly 320 may include one or more LED Drivers 372 and/or one or more LED Emitters 374 (which have a representative 810 nm wavelength). In these embodiments, the microcontroller 317 may provide power to the MICS transceiver 325 and may also receive and/or transmit commands, data and/or instructions to the MICS transceiver 325. In exemplary embodiments, the MICS transceiver 325 may include a MICS antenna 326 which communicates with the MICS transceiver 360 in the medical implant assembly through the MICS antenna 361. In exemplary embodiments, the MICS transceiver 360 may be coupled and/or connected to the implant medical device 355 and provide instructions, commands and/or data and may receive medical implant device 355 status and/or parameters which may be transmitted off of the medical implant assembly as described above and below. In exemplary embodiments, the MICS transceiver 360 may also communicate with the battery charging circuit or controller 347 and/or the rechargeable battery to receive battery status parameters as has been described. In exemplary embodiments, the LED assembly (or plurality of LED lights) 320 may transmit a plurality of light beams to the photovoltaic assembly or plurality of photovoltaic cells 345 in the medical implant assembly. In exemplary embodiments, the photovoltaic assembly or plurality of photovoltaic cells 345 may convert the light beams into electrical energy and transfer or provide the electrical power to the battery charging controller or circuit 347.

Figure 4:
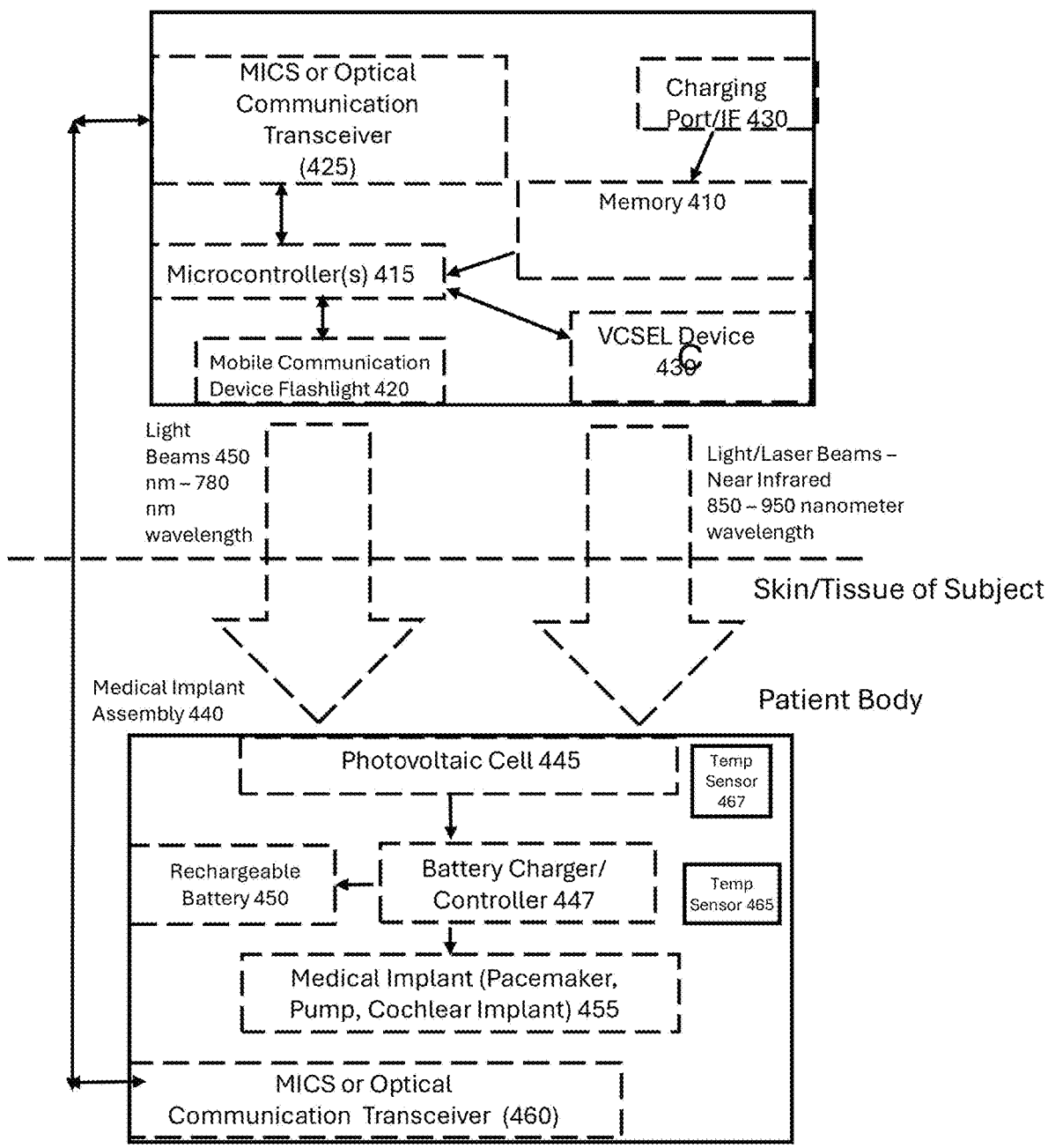
FIG. 4 illustrates a system for emergency optical charging of the rechargeable battery in the medical implant assembly.

In some cases, emergency charging of the rechargeable battery 250 in the medical implant assembly 240 may be necessary when a charge level has gotten too low. In some cases, the charging assembly 210 (including the one or more LED assemblies 220) may not be available to provide the charging of the rechargeable battery 250 in the medical implant assembly 240. In these cases, lighting assemblies in a mobile communication or computing device may be utilized for emergency charging or quick charging. In these embodiments, light having a wavelength of 400-700 nanometers may penetrate the subject's tissue and may be received by the one or more photovoltaic cells 445, although the wavelength range and/or absorption by molecules may limit the amount of light received by the one or more photovoltaic cells 445. According, the charge delivered to the battery charger controller 447 which in turn charges the rechargeable battery 450, however to a lower level of charge. This can be utilized in emergency situations. FIG. 4 illustrates a system for emergency optical charging of the rechargeable battery 450 in the medical implant assembly. In FIG. 4, the mobile communication or computing device 405 may become the charging assembly. In exemplary embodiments, the mobile communication or computing device 405 may include one or more MICS or optical communication transceivers 425, one or more memory devices 410, computer-readable instructions stored in the one or more interfaces 430, one or more microcontrollers 415, a mobile communication device flashlight or LED assembly or device 420 and/or one or more Vertical Cavity Surface Emitting Laser devices 430. In exemplary embodiments, the computer-readable instructions may be executable by the one or more microcontrollers to perform operations and functions of the subject matter described herein. In exemplary embodiments, the mobile communication device flashlight or LED assemblies 420 may emit light beams at between 450 nanometers to 780 nanometers (or alternatively between 400 nanometers to 700 nanometers. In some cases, this may be green light, red light, white light or blue light. In exemplary embodiments, the mobile communication device flashlight or LEDs 420 may be controlled by the one or more microcontrollers 415 in the mobile communication and computing device 405. In this case, the light beams emitted by the mobile communication device flashlight or LEDs 420 may provide emergency charging to the rechargeable battery 350 (through the one or more photovoltaic cells 445 and/or a battery charger controller 447) until the rechargeable battery 450 can be charged for a longer period of time by a charging assembly 410. The mobile communication device flashlight or LEDs may include a plurality of LEDs (or other lighting assemblies) that are utilized to perform the flashlight function on the mobile communication or computing device 405. In other embodiments, emergency charging may occur through one or more vertical cavity surface emitting laser (VCSEL) devices 430 in the mobile communication or computing device 405. One or more VCSEL devices 430 in the mobile communication device 405 are existing devices or lasers in the mobile communication or computing device 405 and may be utilized for gesture recognition, facial ID recognition and/or autofocus for the camera in the mobile communication device 405. In exemplary embodiments, the one or more VCSEL devices 430 may be controlled via one or more processors or microcontrollers 415 and the one or more VCSEL devices 430 may emit near infrared light beams or laser beam(s) ranging from 850 to 950 nanometers. In exemplary embodiments, the one or more VCSEL devices 430 may emit laser light beams (or other light beams) to the one or more photovoltaic cells 445, which supply electrical power to the battery charger controller 447, which in turn provides electrical power and/or charging to the rechargeable battery 450. Thus, the one or more VCSEL devices 430 may provide emergency charging to the rechargeable battery 450 in the medical implant assembly 440 when normal charging is not possible. The other components illustrated in FIG. 4 may operate in similar fashion with similar features as those described in FIGS. 2A-2C and 3A-3C.

Figure 5:
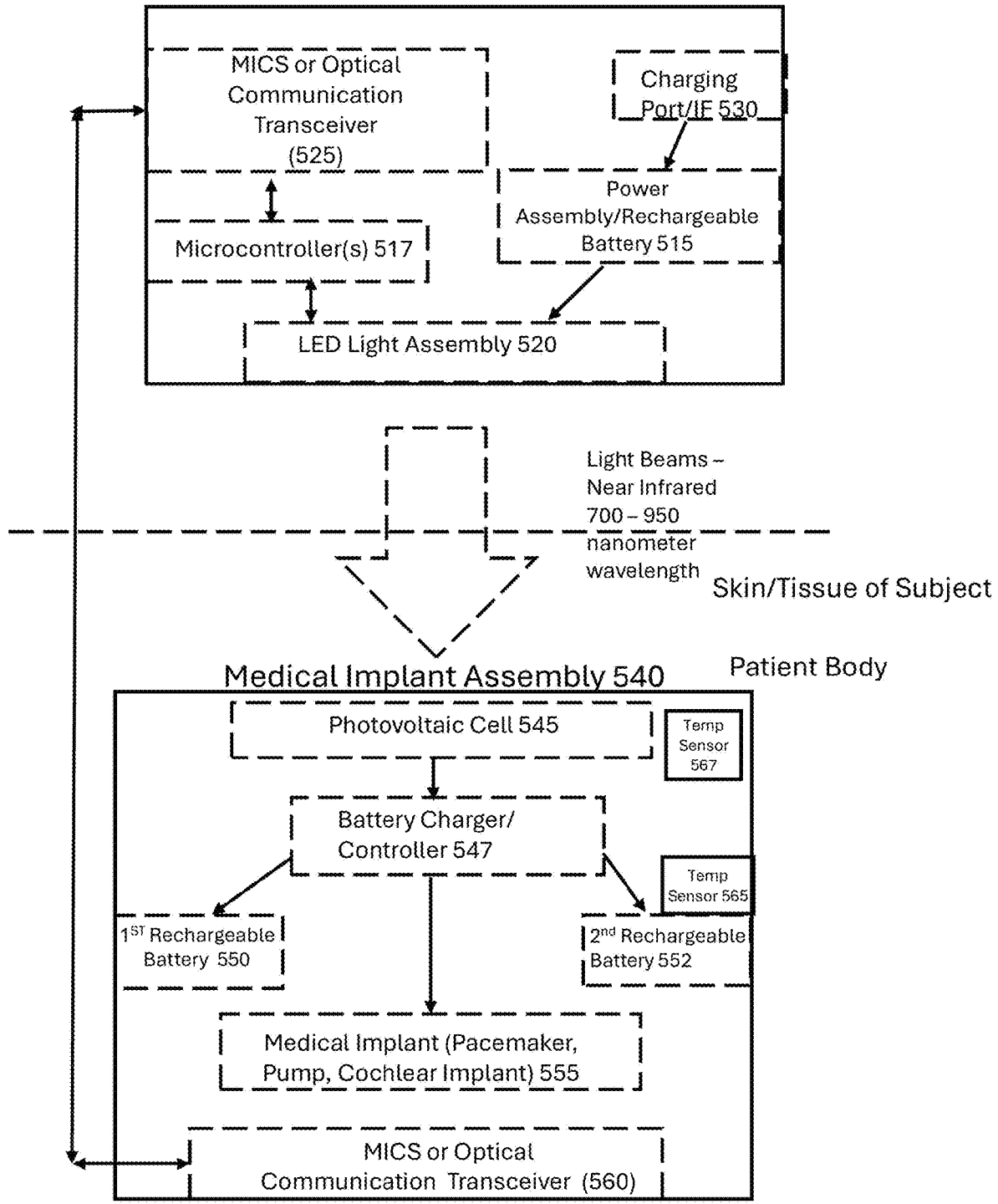
FIG. 5 illustrates a block diagram for an optical power system including a charging assembly and a medical implant assembly including two rechargeable batteries according to exemplary embodiments.

Because medical implant devices are so important to the subject, it is also beneficial to include two batteries in the medical implant assembly in order to enhance the medical implant assembly's life and operational capability. FIG. 5 illustrates a block diagram for an optical power system including a charging assembly and a medical implant assembly including two rechargeable batteries according to exemplary embodiments. Two batteries are beneficial when the system is looking to store more power for longer periods and charge it slowly to extend battery life. In exemplary embodiments, slow charging prevents rapid degradation of the batteries, ensuring that the rechargeable batteries last longer. In addition, by managing the load across two rechargeable batteries, you can control the current flow and reduce the stress on each individual rechargeable battery. In exemplary embodiments, distributing the charging between two batteries can prevent overheating and ensure that each battery is charged within safe limits, thereby allowing for slow, consistent charging. Rechargeable batteries, such as Lithium-ion (Li-ion), Lithium-polymer (LiPo), Nickel-Metal Hydride (NiMH), and Lead-Acid batteries, degrade over time due to various factors, including charge-discharge cycles, temperature fluctuations, and improper charging methods. The maximum number of charging cycles before significant capacity loss is a key limitation, impacting battery longevity and performance. Typical causes of capacity loss are over charging and deep discharging, fast charging and over current draw, and thermal stress. Using two batteries and switching between them can help enhance battery longevity, efficiency, and performance. The technique avoids deep discharges and reduces charge cycle wear In FIG. 5, the charging assembly (or flexible adhesive package) 510 includes the MICS wireless transceiver or optical communication transceiver 525, the charging port or interface 530, the power assembly or rechargeable battery 515, the one or more microcontrollers 517 and/or the one or more LED light assemblies 520. These components operate the same as described above with respect to FIGS. 2A-2C and FIGS. 3A-3C (and may provide the same features as discussed above) and will not be described further here. The operations described in FIG. 4 may also be utilized with the functions and features described here with respect to FIG. 5.

In exemplary embodiments, the medical implant assembly 540 includes one or more photovoltaic cells 545, one or more battery charger controllers 547, a first rechargeable battery 550, a second rechargeable battery 552, one or more temperature sensors 565 and 567, a medical implant device 555, and/or a MICS wireless transceiver (or optical communication transceiver) 560. In exemplary embodiments, the one or more photovoltaic cells or the photovoltaic assembly 545 may convert the light beams received from the one or more LED light assemblies 520 into electrical energy. In exemplary embodiments, the one or more photovoltaic cells 545 may transfer the electrical energy to the battery charger controller 547. In exemplary embodiments, the battery charger controller 547 may be coupled and/or connected to the first rechargeable battery 550 and/or the second rechargeable battery 552. In exemplary embodiments, the battery charger controller 547 may charge the first rechargeable battery 550 and/or the second rechargeable battery 552 after receiving the electrical power. In exemplary embodiments, the battery charger controller 547 (and/or the first rechargeable battery 550 and/or the second rechargeable battery 552) may provide power to the medical implant device 555 (and other components of the medical implant assembly such as the MICS wireless transceiver (or optical communication transceiver) 560, the temperature sensors 565 and 567 and/or the one or more photovoltaic cells 545. In exemplary embodiments, the temperature sensors 565 may monitor temperatures of the first rechargeable battery 550 and/or the second rechargeable battery 552 (as well as the skin or tissue of the subject or patient) and may communicate with the battery charger controller 547 to minimize charging or deactivate charging if the temperature is too high (or to communicate with the microcontroller 517 in the charging assembly 510 (via the MICS wireless transceivers 560 and 525) in order to reduce or eliminate the light beams being transmitted by the one or more LED light assemblies 520. In exemplary embodiments, the one or more temperature sensors 567 may monitor temperature in the one or more photovoltaic cells 545 or the patient's skin or tissue in order to turn on and off the photovoltaic cells or LED light assemblies if the temperature is too high. The two rechargeable batteries 550 552 may also be utilized in the embodiments discussed above in FIG. 2A-20, 3A-3B or 4.

Figure 6:
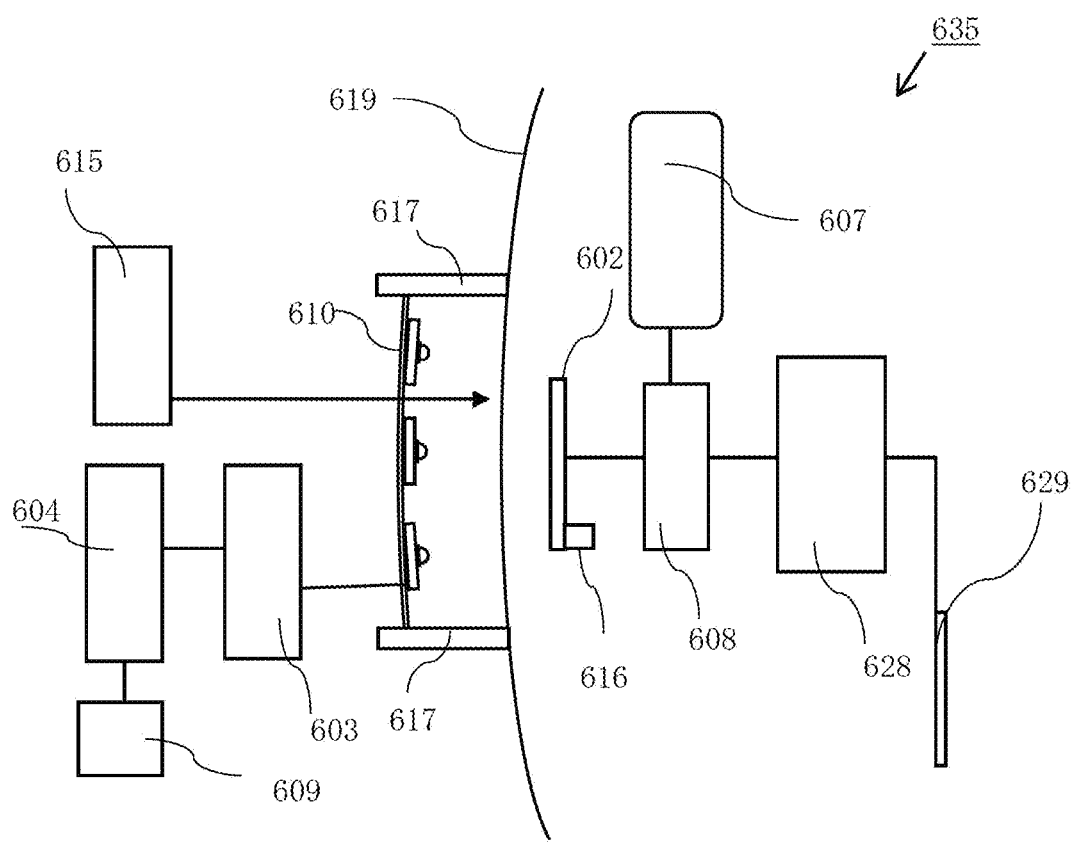
FIG. 6 illustrates a block diagram of a physical embodiments of the optical power system according to exemplary embodiments.

FIG. 6 illustrates a block diagram of a physical embodiments of the optical power system according to exemplary embodiments. In exemplary embodiments, the charging assembly or flexible package assembly may include a wireless communication transceiver 609, a controller or microcontroller 604, one or more thermal sensors 615, one or more LED driver circuits or assemblies 603, one or more LED arrays 610 (including three visible LEDs), and/or one or more LED light shields 617 to prevent the LED light from escaping the target area. In exemplary embodiments, the one or more thermal sensors 615 may monitor temperature in an area around the one or more LED arrays 610 or other components of the charging assembly or flexible package device). In exemplary embodiments, the controller 604 may be coupled to the wireless communication transceiver 609 to receive commands, measurements and/or instructions. In exemplary embodiments, the controller 604 may be coupled to the LED driver circuit 603. In exemplary embodiments, the LED driver circuit 603 may receive commands or instructions from the controller 604 and may activate and/or deactivate the one or more LED arrays 610, which transmits the light to the medical implant assembly. Computer-readable instructions may be executable by the one or more controllers to perform the operations described above.

In exemplary embodiments, the medical implant assembly may include one or more photovoltaic cells 602, one or more thermal or temperature sensors 616, one or more rechargeable batteries 607, one or more battery controllers (or battery charger controller) 608, and/or a medical implant device (e.g., cardiac pacemaker) 628 and/or a lead 629 for the medical implant device. In exemplary embodiments, the one or more photovoltaic cells 602 may receive the light beams transmitted from the one or more LED arrays 610 and convert the light beams into electrical energy. In exemplary embodiments, the electrical energy is transferred to the battery charger controller 608. In exemplary embodiments, the battery charger controller 608 may charge the one or more rechargeable batteries 607. In exemplary embodiments, the one or more rechargeable batteries 607 and/or the battery charger controller 608 may provide power to the medical implant device (e.g., cardiac pacemaker circuit) 628 and/or a pacemaker lead 629. The techniques and/or components described in FIG. 6 may be utilized in the system and methods described in FIGS. 2A-20, 3A-3B, 4, AND 5.

In some embodiments, the medical implant device may be located further inside the subject's skin and thus there may be a need for intermediate devices to assist in delivering the optical power to the medical implant device. These intermediate optical power substations may "relay" power to medical implant devices and/or assemblies deeper in the subject's tissue. In these embodiments, the charging assembly or flexible adhesive package may charge the first optical substation or implant optical repeater devices to relay power to other optical substations (or repeater devices) which then relay the optical wireless power to the medical implant assembly. Although only one intermediate substation is shown, multiple intermediate substations may be used in such an optical power delivery system if the medical implant assembly is located further into the subject or patient's body or tissue. In exemplary embodiments, the one intermediate substation may have one or more photovoltaic cells, a battery charging controller, a rechargeable battery, and/or one or more LED light assemblies or laser light assemblies. The LED light assemblies or laser light assemblies may be pointed to the medical implant assembly or the next intermediate substation to deliver the optical power to a destination medical implant device. In exemplary embodiments, the intermediate optical power substation or optical power repeater assemblies 775 may be located under a patient or subject's skin or within the subject's tissue.

Figure 7:
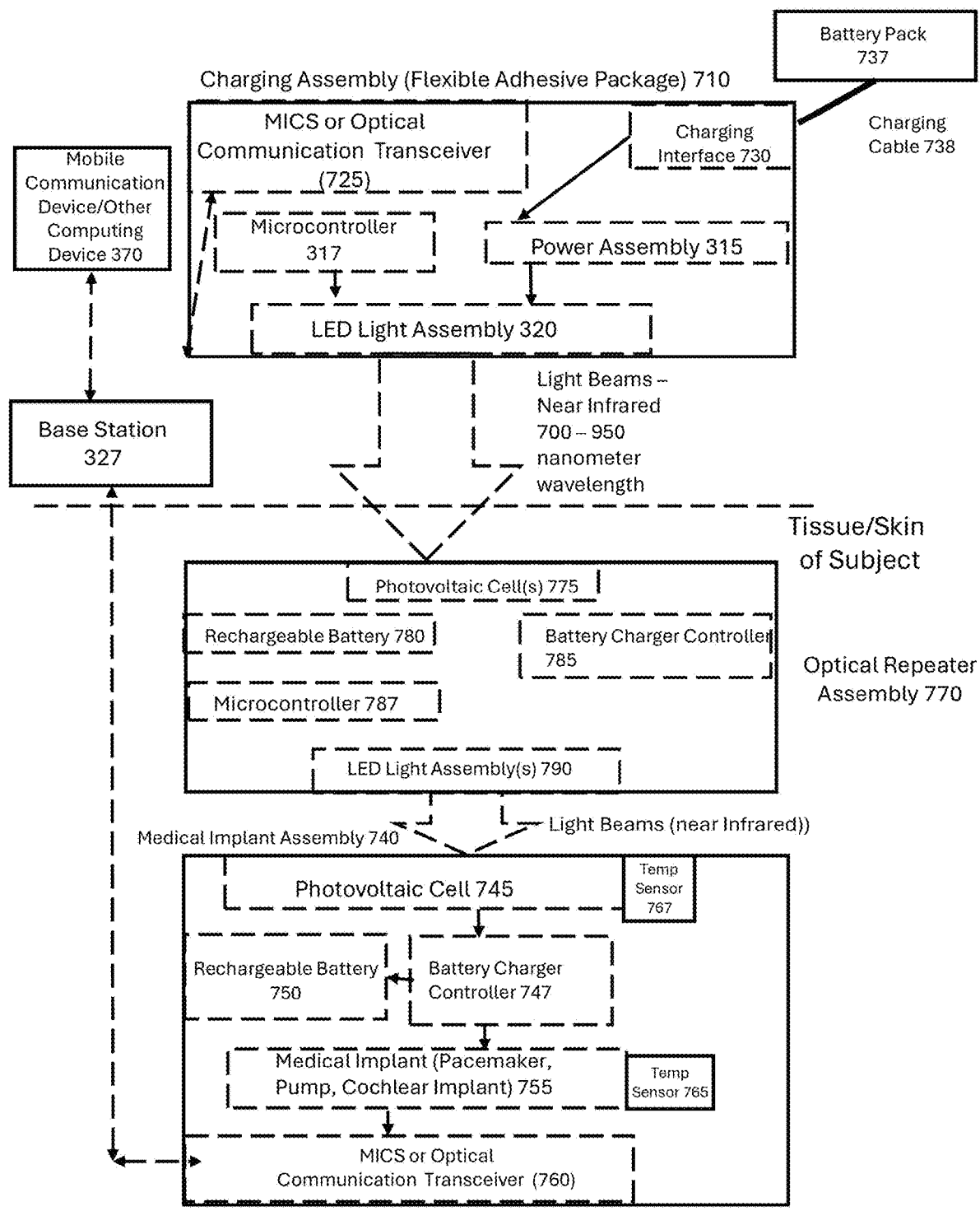
FIG. 7 illustrates a block diagram of an optical power system including a charging assembly, an intermediate optical power substation and/or a medical implant assembly according to exemplary embodiments.

FIG. 7 illustrates a block diagram of a optical power system including a charging assembly, an intermediate optical power substation and/or a medical implant assembly according to exemplary embodiments. As an illustrative example, the charging assembly/flexible adhesive package 710 may be placed on a subject's skin and the optical repeater assembly or intermediate optical power substation 770 may be positioned 7 millimeters deep in a patient's skin whereas the medical implant assembly 740 is 13 millimeter to 14 millimeter deep. Other distances may be utilized for the location or positioning of the intermediate optical power substation 770 and this is only a representative example. FIG. 7 illustrates an optical power delivery system for a medical implant assembly including one intermediate substation for relaying power according to exemplary embodiments. In exemplary embodiments, the optical implant delivery system may include a charging assembly (or flexible adhesive package) 710, an intermediate optical power substation or repeater assembly 770, and/or a medical implant assembly 740. As discussed previously, although only one intermediate optical power substation or repeater assembly 770 is shown, multiple intermediate optical power substation or repeater assemblies 770 may be utilized depending on the application and/or location of the medical implant assembly 740 within the subject. In exemplary embodiments, the charging assembly or flexible adhesive package 710 may include a MICS wireless communication transceiver 725 (or optical communication transceiver 725), a charging interface 720, a microcontroller 717, a power assembly 715, and one or more LED light assemblies 720. In exemplary embodiments, the charging assembly or flexible adhesive package 710 may be powered by one or more battery packs 727 through a charging cable 738. These components operate in the same fashion as components in the charging assemblies or flexible adhesive packages described in FIGS. 2A-20, 3A-3C, 4, 5 and 6 and can be utilized in embodiments such as those described in FIGS. 2A-20, 3A-3C, 4, 5 and 6.

In exemplary embodiments, the one or more LED light assemblies 720 may transmit a plurality of light beams (e.g., which may have a wavelength ranging from 700 to 950 nanometer wavelength). In exemplary embodiments, the intermediate optical power substation or repeater assemblies 770 may receive the plurality of light beams and transmit a plurality of intermediate light beams to the medical implant assembly 740. In exemplary embodiments, the intermediate optical power substation or repeater assembly 770 may include one or more intermediate photovoltaic cells or assemblies 775, one or more rechargeable batteries 780, a battery charger controller 785, one or more microcontrollers 787 and/or one or more intermediate LED light assemblies or cells 790. In these embodiments, the one or more intermediate photovoltaic cells or assemblies 775 may convert the plurality of light beams transmitted by the LED light assemblies 720 into electrical energy. In exemplary embodiments, one or more intermediate photovoltaic cells 775 may transfer the electrical energy to the battery charger controller 785. In exemplary embodiments, the battery charger controller 785 may provide the electrical power to the one or more rechargeable batteries 780 to charge the rechargeable batteries 780. In exemplary embodiments, the battery charger controller 785 and/or the one or more rechargeable batteries 780 may provide power to the one or more microcontrollers 787 and/or the one or more intermediate LED light assemblies 790. In exemplary embodiments, the one or more microcontrollers 787 may control operations of the intermediate optical power substation or optical repeater assembly 770. In exemplary embodiments, the one or more microcontrollers 787 may transmit instructions and/or commands to the intermediate LED light assemblies 790 to generate a plurality of intermediate light beams. In exemplary embodiments, the intermediate LED light assemblies 790 may generate the plurality of intermediate light beams further into the subject or patient's tissue. In exemplary embodiments, computer-readable instructions executable by the one or more microcontrollers may cause components of the intermediate optical power substations or repeater assemblies 770.

In exemplary embodiments, the intermediate LED light assemblies 790 may transmit a plurality of intermediate light beams to the medical implant assembly 740. In exemplary embodiments, the medical implant assembly 740 may include one or more photovoltaic cells 745, one or more rechargeable batteries 750, a battery charger controller 747, a medical implant device 755, a MICS wireless transceiver 760 (or an optical communication transceiver) and/or one or more temperature sensors 765 or 767. The medical implant assembly 740, the medical communication device and other computing device 370 and/or the MICS or other communication base station 727 may operate in the same fashion as the medical implant assemblies described in FIGS. 2A-2C, 3A-3B, 4, 5 and 6. This intermediate optical power substation or optical repeater assembly 770 may allow coverage for providing optical power to medical implant devices that are located deeper in a patient's tissue and/or farther away from the charging assembly or flexible adhesive package.

In some embodiments, solar light beams may be able to provide power to medical implant devices that are implanted on a subject's skin or just under the subject's skin. There may be two potential use cases. In exemplary embodiments, a medical implant that is in a part of the body that is exposed to ambient light (like the head, arm, leg, etc.), may be able to be charged via solar light beams. In these embodiments, such a medical implant device may be charged by the sun or any ambient light that gets through the skin and tissue. Obviously, the implant cannot be too deep into the skin otherwise not enough light will get to it. In some embodiments, solar charging may be utilized for implants that are implanted on the skin surface or from a depth ranging from 0 to 5 mm depth in a patient or subject's tissue. Although solar laser light beams include ultraviolet light, infrared light, the subject matter described herein may utilize visible light wavelengths. In exemplary embodiments, these visible light wavelengths may range from 400 nm to 700 nm. Thus, LED light assemblies with these visible wavelengths may be utilized in the subject matter described in FIG. 8 and the related disclosure. The ultraviolet and infrared wavelengths may also be utilized, but do not have the charging capabilities of the visible light wavelengths.

A second use case may be an implanted identification chip, such as an RFID chip as the medical implant assembly, which is inserted or implanted under a patient's skin. The identification chip may store information store and access information, and can be used for a variety of purposes, including identification, payments, and healthcare of the subject. In exemplary embodiments, the solar light and/or other ambient light may be utilized to charge the implanted identification chip. The identification chip may a RFID chip, which may include a transponder that contains a unique ID number and/or a near field communication (NFC) chip. These implanted chips may be utilized for a) Identification or to verify identity for access to systems like doors, transit, and social media; b) Healthcare or to store medical information, such as allergies, medications, and past antibiotic usage; c) Payments or utilized for contactless payments; d) Device control or automatically controlling other devices; or e) tracking or tracking patients with dementia or tracking newborns to eliminate swapping and/or kidnapping.

Figure 8:
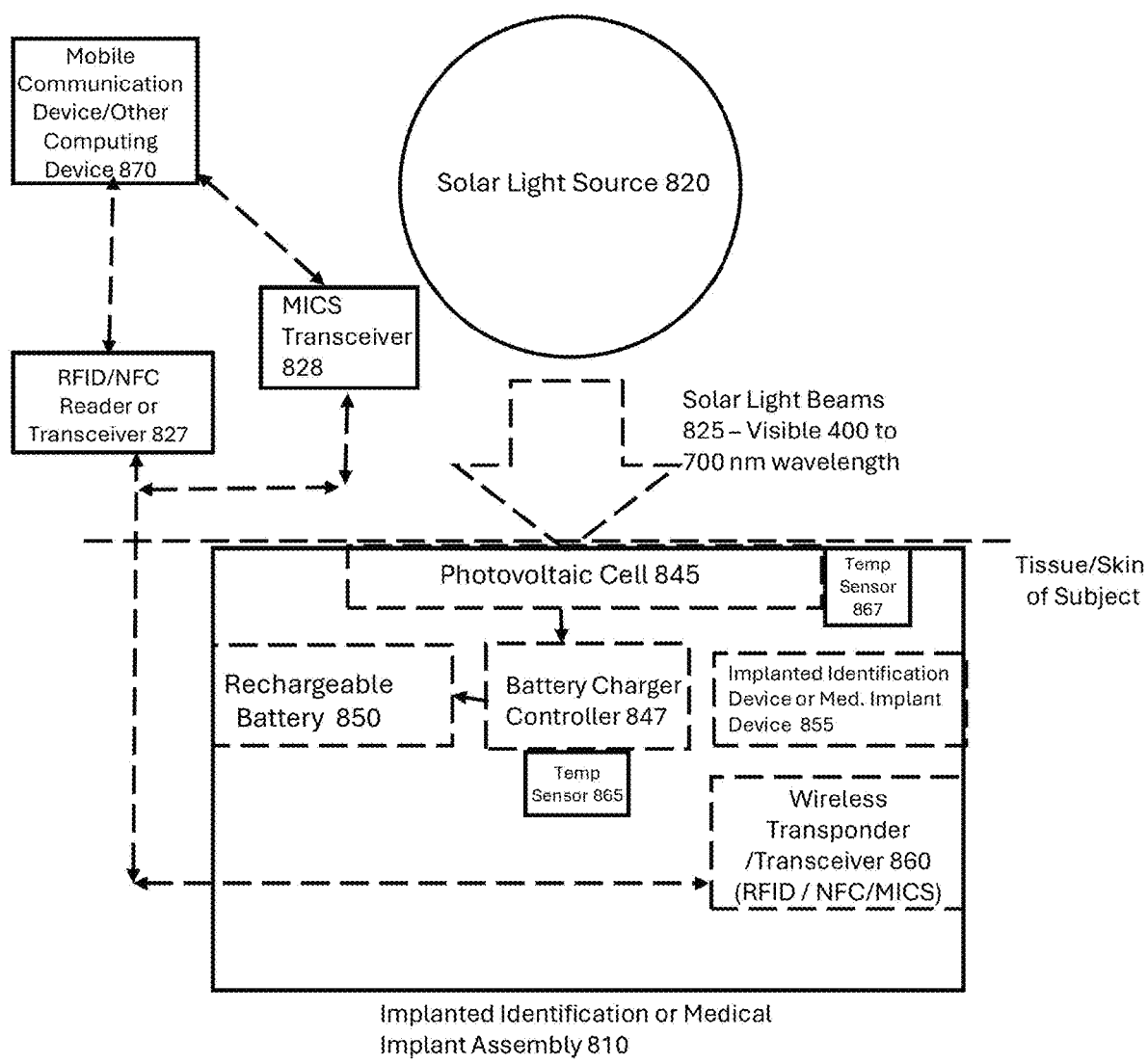
FIG. 8 illustrates an optical power system for charging an identification chip or electronic assembly according to exemplary embodiments.

FIG. 8 illustrates an optical power system for charging an identification chip or medical implant assembly according to exemplary embodiments. In exemplary embodiments, a solar light source 820 (or other ambient light source) may transmit a plurality of solar light beams 825 to the implanted identification device or medical implant assembly 810. In exemplary embodiments, the implanted identification assembly or medical implant assembly 810 may include one or more photovoltaic cells or assemblies 845, one or more temperature sensors 865 or 867, an implanted identification device or medical implant device 855 including one or more microcontrollers and/or memory devices, one or more rechargeable batteries 850, a battery charger controller 847, and a wireless transceiver or transponder 860. In exemplary embodiments, one or more photovoltaic cells or assemblies 845 of implanted identification assembly or medical implant assembly 810 may receive the plurality of solar light beams and convert these to electrical energy. In exemplary embodiments, the one or more photovoltaic cells 845 may transfer the electrical power or energy to the battery charger controller 847. In exemplary embodiments, the battery charger controller 847 may charge the one or more rechargeable batteries 850. In exemplary embodiments, the battery charger controller 847 and/or the one or more rechargeable batteries 850 may provide electrical power to the implantable identification device or implanted medical device 855, the one or more temperature sensors 865 or 867 and/or the wireless transponder/transceiver 860. In exemplary embodiments, the implantable identification device or implanted medical device 855 may store identification, payment, tracking, device control or healthcare information in the one or more memory devices. In exemplary embodiments, the controller or processor in the implantable identification device or medical implant device 855 may control operations of the implantable identification assembly or medical implant device. In exemplary embodiments, the implanted identification device or medical implant device 855 may communicate with outside devices utilizing a wireless transponder or transceiver 860 (which may be an RFID transponder or a NFC transponder—or a MICS communication transceiver). In exemplary embodiments, the wireless transponder or transceiver 860 may transmit the information identified above (identification, payment, tracking, device control or healthcare information) to a reader assembly 827 (or wireless transceiver 828) which may pass the implanted identification device's information or the medical implant assembly's status parameters and/or patient information or physiological parameters to a mobile communication device or other computing device 870 which may then utilize the retrieved information. The temperature sensors 865 or 867 may monitor temperature of the components of the implanted identification assembly or medical implant assembly 810 and may utilize the controller in the implanted identification device or medical implant device 855 and/or the wireless transponder or transceiver 860 to identify that the implanted identification assembly or medical implant device 810 should be moved out of the sunlight or that the one or more photovoltaic cells 845 or battery charger controller may need to be deactivated.

Figure 9:
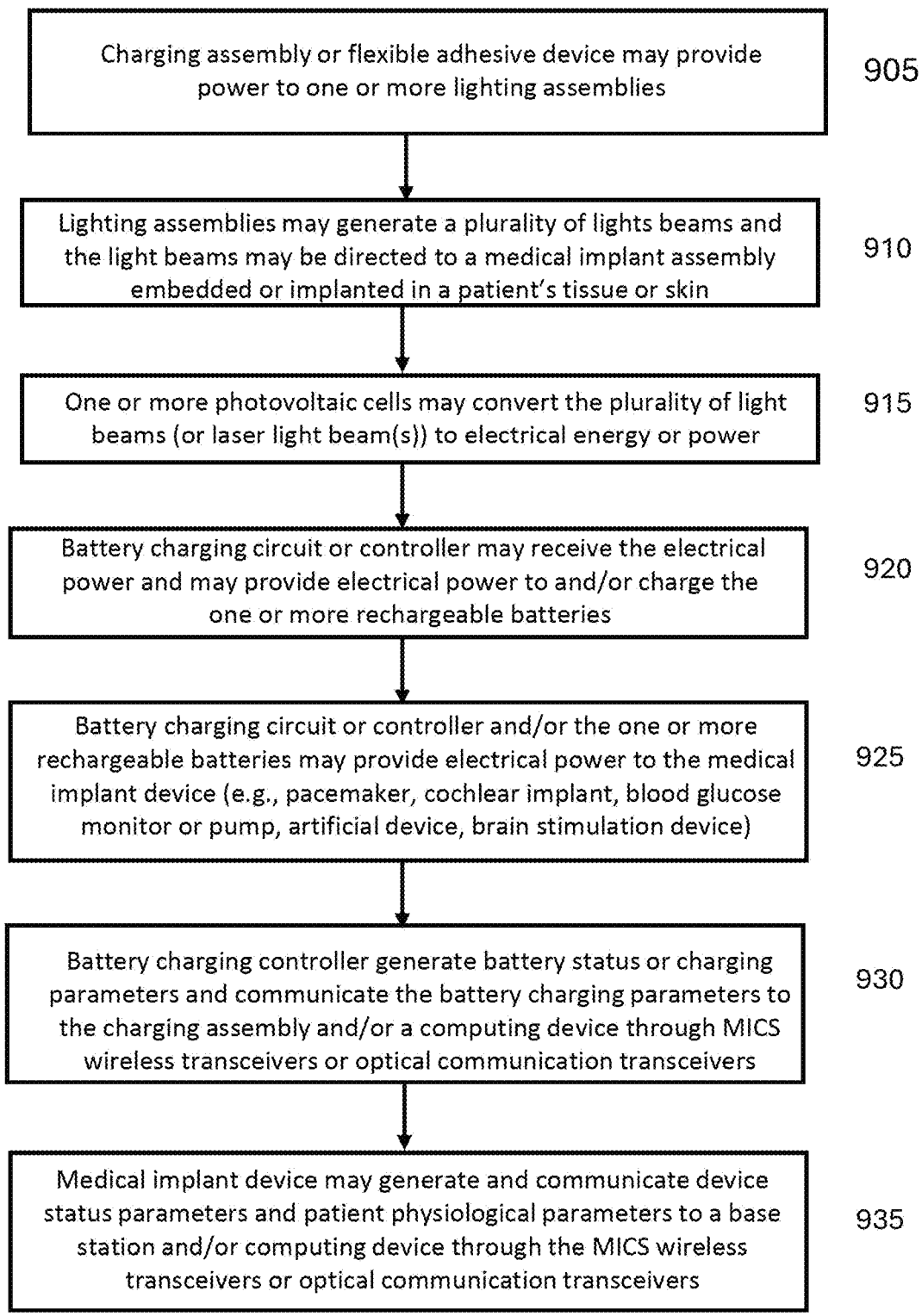
FIG. 9 illustrates a flowchart of providing optical power to rechargeable battery(s) in a medical implant assembly according to exemplary embodiments.

FIG. 9 illustrates a flowchart of providing optical power to rechargeable battery(s) in a medical implant assembly according to exemplary embodiments. In exemplary embodiments, in step 905, a charging assembly or flexible adhesive device may provide power to one or more lighting assemblies. The providing of power to the lighting assemblies is described in FIGS. 2A-20, 3A-3C, and 5-7. In addition, as described in FIG. 4, a mobile communication device power supply may provide power to lighting assemblies such as a mobile device flashlight or LEDs and/or to VCSEL devices. In exemplary embodiments, in step 910, the lighting assemblies may generate a plurality of lights beams and the light beams may be directed to a medical implant assembly embedded or implanted in a patient's tissue or skin. The light beams generated may be near infrared light beams (e.g., 700 to 900 nm wavelength), visible light beams (e.g., 400 to 700 nm wavelength), laser light beam(s) from VCSEL devices (e.g., 850 to 950 nm wavelength). In some embodiments, as described in FIG. 8, solar light beams may be transmitted or directed to the medical implant assembly for charging the medical implant assembly. In exemplary embodiments, in step 915, one or more photovoltaic cells may convert the plurality of light beams (or laser light beam(s)) to electrical energy or power. In exemplary embodiments, in step 920, the electrical energy or power may be transferred or provided to a battery charging circuit or controller. In exemplary embodiments, in step 920, the battery charging circuit or controller may receive the electrical power and may provide electrical power to and/or charge the one or more rechargeable batteries. In exemplary embodiments, in step 925, the battery charging circuit or controller and/or the one or more rechargeable batteries may provide electrical power to the medical implant device (e.g., pacemaker, cochlear implant, blood glucose monitor or pump, artificial device, brain stimulation device). In exemplary embodiments, in step 930, the battery charging controller may generate battery status or charging parameters and communicate the battery charging parameters to the charging assembly and/or a computing device through MICS wireless transceivers or optical communication transceivers. In exemplary embodiments, in step 935, the medical implant device may generate and communicate device status parameters and patient physiological parameters to a base station and/or computing device through the MICS wireless transceivers or optical communication transceivers. The method described in FIG. 9 may be utilized with the systems or devices described in FIGS. 1-8.

While various embodiments described in the present disclosure have been described above, it should be understood that they have been presented by way of example, and not limitation. It is to be understood that various changes in form and detail can be made therein without departing from the scope of the present disclosure. In addition to using hardware (e.g., within or coupled to a central processing unit ("CPU"), microprocessor, micro controller, digital signal processor, processor core, system on chip ("SOC") or any other device), implementations may also be embodied in software (e.g. computer readable code, program code, and/or instructions disposed in any form, such as source, object or machine language) disposed for example in a non-transitory computer-readable medium configured to store the software. Such software can enable, for example, the function, fabrication, modeling, simulation, description and/or testing of the apparatus and methods describe herein. For example, this can be accomplished through the use of general program languages (e.g., C, C++), hardware description languages (HDL) including Verilog HDL, VHDL, and so on, or other available programs. Such software can be disposed in any known non-transitory computer-readable medium, such as semiconductor, magnetic disc, or optical disc (e.g., CD-ROM, DVD-ROM, etc.). The software can also be disposed as computer data embodied in a non-transitory computer-readable transmission medium (e.g., solid state memory any other non-transitory medium including digital, optical, analog-based medium, such as removable storage media). Embodiments of the present disclosure may include methods of providing the apparatus described herein by providing software describing the apparatus and subsequently transmitting the software as a computer data signal over a communication network including the internet and intranets.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

The invention claimed is:

1. An optical wireless power delivery system to provide power to a medical implant device, comprising:
   a battery pack configured to generate electrical power and to transmit the generated electrical power to a cable;
   a flexible adhesive device attached to a subject's skin, the flexible adhesive device including:
      one or more LED light assemblies configured to transmit a plurality of light beams to a skin or tissue of the subject;
      a first Medical Implant Communication System (MICS) wireless transceiver configured to communicate with a medical implant assembly and/or a base station to receive rechargeable battery status parameters of the medical implant assembly;
      one or more microcontrollers configured to control operations of components of the flexible adhesive device; and
      a port electrically connected to the cable to receive the electrical power and to provide power to one or more microcontrollers or processors, the one or more LED light assemblies and the first MICS wireless communication transceiver, the plurality of light beams have a near infrared wavelength ranging from 700 to 950 nanometers (nm); and
   the medical implant assembly including:
      the medical implant device implanted in the tissue of the subject;
      a rechargeable battery configured to provide power to the medical implant device and other components of the medical implant assembly;
      a photovoltaic assembly configured to convert the plurality of light beams transmitted by the one or more LED light assemblies to electrical power to charge a battery charger controller;
      the battery charger controller configured to charge the rechargeable battery and/or to provide power to the medical implant device; and
      a second MICS wireless transceiver configured to communicate the rechargeable battery status parameters of the metical implant assembly to the base station and/or the first MICS wireless transceiver.

2. The optical wireless power delivery system of claim 1, wherein the plurality of light beams are modulated light beams.

3. The optical wireless power delivery system of claim 1, wherein the battery pack has a greater electrical power than the rechargeable battery in the medical implant assembly.

4. The optical wireless power delivery system of claim 1, wherein the flexible adhesive device utilizes medical securement tape.

5. The optical wireless power delivery system of claim 1, wherein the one or more LED light assemblies transmit the plurality of light beams with a wavelength of 730 nm to 830 nm.

6. The optical wireless power delivery system of claim 1, wherein the plurality of light beams has an intensity ranging from 50 to 150 $mW/cm^2$.

7. The optical wireless power delivery system of claim 1, further including one or more temperature sensors, the one or more temperature sensors configured to monitor temperature of the tissue of the subject, the one or more rechargeable batteries or the medical implant device.

8. The optical wireless power delivery system of claim 1, wherein a depth from the subject's skin for the medical device implant ranges from 1 millimeter (mm) to 15 mm.

9. The optical wireless power delivery system of claim 1, wherein a number of LED lights in the one or more LED assemblies ranges from 1 LED light to 30 LED lights.

10. The optical wireless power delivery system of claim 1, wherein the photovoltaic assembly includes a surface optical coating on photovoltaic cells of the photovoltaic assembly, the surface optical coating configured to minimize a reflection of the plurality of light beams.

11. An optical wireless power delivery system to provide power to a medical implant assembly in the subject, comprising:
   a charging assembly including:
      one or more LED light assemblies configured to transmit a plurality of light beams to a skin of the subject;
      a rechargeable power supply configured to provide power to the charging assembly;
      a charging port, (a USB-C port or an AC adapter port) electronically coupled to the rechargeable power supply to receive external power to charge the rechargeable power supply; and
      a first Medical Implant Communication System (MICS) wireless transceiver configured to communicate with the medical implant assembly and/or a base station to provide status of a rechargeable battery in the medical implant assembly;
   wherein the charging assembly is integrated into a flexible adhesive patch configured to be attached to the skin of the subject and wherein the plurality of light beams have a near infrared wavelength ranging from 700 to 950 nanometers (nm); and
   the medical implant assembly including:
      the medical implant device (pacemaker, cochlear ear implants, blood glucose/insulin pump or monitor) implanted in the subject;
      the rechargeable battery configured to provide power to the medical implant device and other components of the medical implant assembly;

a battery charger controller configured to charge the rechargeable battery and to provide electrical power to the medical implant device;

one or more photovoltaic cells configured to convert the plurality of light beams transmitted by the one or more LED light assemblies to electrical power to charge the rechargeable battery; and a second MICS wireless transceiver configured to communicate a status of the rechargeable battery and other medical implant device parameters of the metical implant assembly to the first MICS wireless transceiver or the base station.

12. The optical wireless power delivery system of claim 11, wherein the plurality of light beams are modulated light beams.

13. The optical wireless power delivery system of claim 11, wherein the one or more LED light assemblies transmit the plurality of light beams with a wavelength of 730 nm to 830 nm.

14. The optical wireless power delivery system of claim 11, wherein the plurality of light beams has an intensity ranging from 50 to 150 mW/cm$^2$.

15. The optical wireless power delivery system of claim 11, further including one or more temperature sensors, the one or more temperature sensors configured to monitor temperature of a tissue of the subject, the one or more rechargeable batteries or the medical implant device.

16. The optical wireless power delivery system of claim 11, wherein a depth from the skin of the subject for the medical implant device ranges from 1 millimeter (mm) to 15 mm.

17. The optical wireless power delivery system of claim 11, wherein the one or more photovoltaic cells includes a surface optical coating on the one or more photovoltaic cells, the surface optical coating configured to minimize a reflection of the plurality of light beams.

18. An optical wireless power system to provide power to a medical implant assembly in the subject, comprising:

a mobile communication or computing device include one or more light assemblies, the one or more light assemblies configured to transmit a plurality of light beams to the medical implant assembly; and the medical implant assembly including:

the medical implant device (pacemaker, cochlear ear implants, blood glucose/insulin pump or monitor) implanted in the subject;

a rechargeable battery configured to provide power to the medical implant device and other components of the medical implant assembly;

a battery charger controller configured to charge the rechargeable battery and to provide electrical power to the medical implant device;

one or more photovoltaic cells configured to convert the plurality of light beams transmitted by the one or more light assemblies in the mobile communication or computing device to electrical power to charge the rechargeable battery; and a Medical Implant Communication System (MICS) wireless transceiver configured to communicate the rechargeable battery status and other medical implant device parameters of the metical implant assembly to the mobile communication or computing device.

19. The optical wireless power system of claim 18, wherein the one or more light assemblies of the mobile communication or computing device are lights utilized by a flashlight function of the mobile communication or computing device and transmit the plurality of light beams having a wavelength of 450 nanometers (nm) to 780 nm to the medical implant assembly.

20. The optical wireless power system of claim 18, wherein the one or more light assemblies of the mobile communication or computing device are vertical cavity surface emitting lasers that transmit the plurality of light beams having a wavelength of 850 nanometers to 950 nanometers to the medical implant assembly.

* * * * *